United States Patent
Reijans et al.

(10) Patent No.: US 9,222,124 B2
(45) Date of Patent: Dec. 29, 2015

(54) METHOD FOR THE SIMULTANEOUS DETECTION OF MULTIPLE NUCLEIC ACID SEQUENCES IN A SAMPLE

(75) Inventors: Martinus Gerardus Cecilia Maria Reijans, Maastricht (NL); Gijs Josephus Henricus Dingemans, Maastricht (NL); Augustinus Franciscus Maria Simons, Maastricht (NL)

(73) Assignee: Pathofinder Holding B.V., Maastricht (NL)

(*) Notice: Subject to any disclaimer, the term of this patent is extended or adjusted under 35 U.S.C. 154(b) by 786 days.

(21) Appl. No.: 12/668,067

(22) PCT Filed: Jul. 10, 2008

(86) PCT No.: PCT/EP2008/059050
§ 371 (c)(1),
(2), (4) Date: Jun. 14, 2010

(87) PCT Pub. No.: WO2009/007438
PCT Pub. Date: Jan. 15, 2009

(65) Prior Publication Data
US 2010/0297630 A1   Nov. 25, 2010

(30) Foreign Application Priority Data
Jul. 11, 2007 (EP) .................................. 07112219

(51) Int. Cl.
*C12P 19/34* (2006.01)
*C12Q 1/68* (2006.01)
(52) U.S. Cl.
CPC .............. *C12Q 1/6818* (2013.01); *C12Q 1/686* (2013.01)

(58) Field of Classification Search
None
See application file for complete search history.

(56) References Cited

U.S. PATENT DOCUMENTS

2006/0281099 A1   12/2006   Breneman et al.

FOREIGN PATENT DOCUMENTS

| EP | 1 130 113 | 9/2001 |
| WO | WO 00/18965 | 4/2000 |
| WO | WO 2004/072301 | 8/2004 |
| WO | WO 2005/059178 | 6/2005 |

OTHER PUBLICATIONS

International Search Report for PCT/EP2008/059050, mailed Nov. 10, 2008.
Written Opinion of the International Searching Authority for PCT/EP2008/059050, mailed Nov. 10, 2008.
(Continued)

*Primary Examiner* — Kenneth Horlick
(74) *Attorney, Agent, or Firm* — Dinsmore & Shohl LLP

(57) ABSTRACT

The invention is in the technical field of detecting nucleic acid sequences in a sample, such as the detection of pathogenic organisms in clinical samples. More specifically, the invention relates to the field of detecting an infection caused by a pathogenic organism such as a virus or a bacterium in a clinical specimen by amplifying and detecting specific nucleic acid sequences from the pathogenic organism. It provides a multiplex assay with the possibility to determine about 30 different target nucleic acid sequences in a single one-tube assay combined with real-time probe detection. The method employs multiplex ligation dependent Probe Amplification (MLPA) employing labelled primers in combination with labelled, probes and detection of the fluorescence.

17 Claims, 11 Drawing Sheets

Overview of the formation of amplicons of a connected probe assembly starting from 2 distinct DNA templates A and B

(56) References Cited

OTHER PUBLICATIONS

Zhang B. et al., "Bacterial Screening Multiplex PCR for *Brucella*, Francisella and Yersinia", Abstracts of the General Meeting of the American Society of Microbiology, The Society, vol. 103, (May 18, 2003), pp. 153.

Worsham, Maria J. et al., "Fine-Mapping Loss of Gene Architecture at the *CDKN2B* ($p15^{INK4b}$), *CDKN2A* ($p14^{ARF}$, $p16^{INK4a}$), and *MTAP* Genes in Head and Neck Squamous Cell Carcinoma", Archives of Otolaryngology—Head and Neck Surgery, vol. 132, No. 4, (Apr. 2006), pp. 409-415.

Ruiz-Point, C. et al., "Duplication and deletion analysis by fluorescent real-time PCR-based genotyping", Clinica Chimica Acta, vol. 363, No. 1-2, (Jan. 2006), pp. 138-146.

Schwartz, D.E. et al., "Time-resolved Förster-resonance-energy-transfer DNA assay on an active CMOS microarray", Biosensors and Bioelectronics, vol. 24, No. 3, (Nov. 15, 2008), pp. 383-390.

Reijans et al "RespiFinder: a New Multiparameter Test to Differentially Identify Fifteen Respiratory Viruses" Journal of Clinical Microbiology, Apr. 2008, vol. 46, No. 4, p. 1232-1240.

Wolffs et al. "Evaluation of MeningoFinder, a Novel Multiplex Ligation-Dependent Probe Amplification Assay for Simultaneous Detection of Six Virus Species Causing Central Nervous System Infections" Journal of Clinical Microbiology, Aug. 2009, vol. 47, No. 8, p. 2620-2622.

Muvunyi et al. "Evaluation of a new multiplex polymerase chain reaction assay STDFinder for the simultaneous detection of 7 sexually transmitted disease pathogens" Diagnostic Microbiology and Infectious Disease 71 (2011) 29-37.

Schouten et al. "Relative quantification of 40 nucleic acid sequences by multiplex ligation-dependent probe amplification" Nucleic Acids Research, 2002, vol. 30, No. 12 e57.

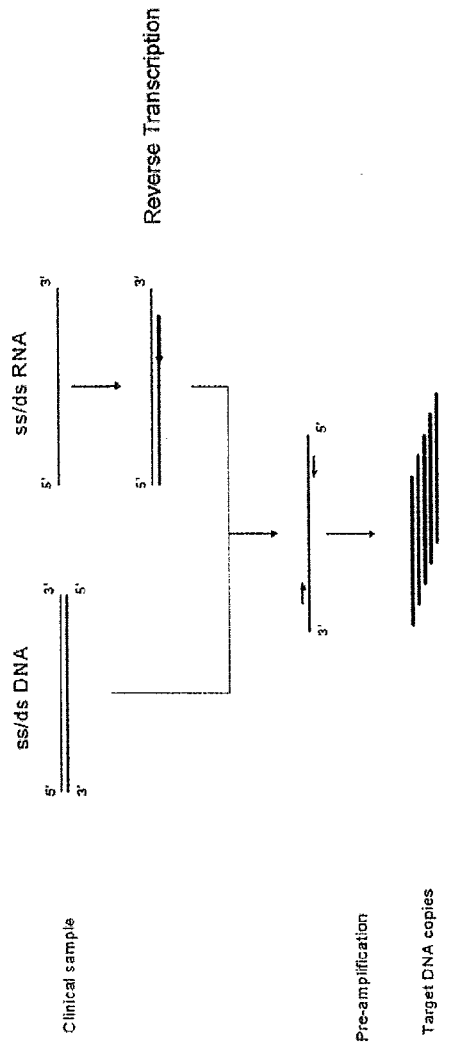
FIGURE 1. The optional reverse transcription and pre-amplification step

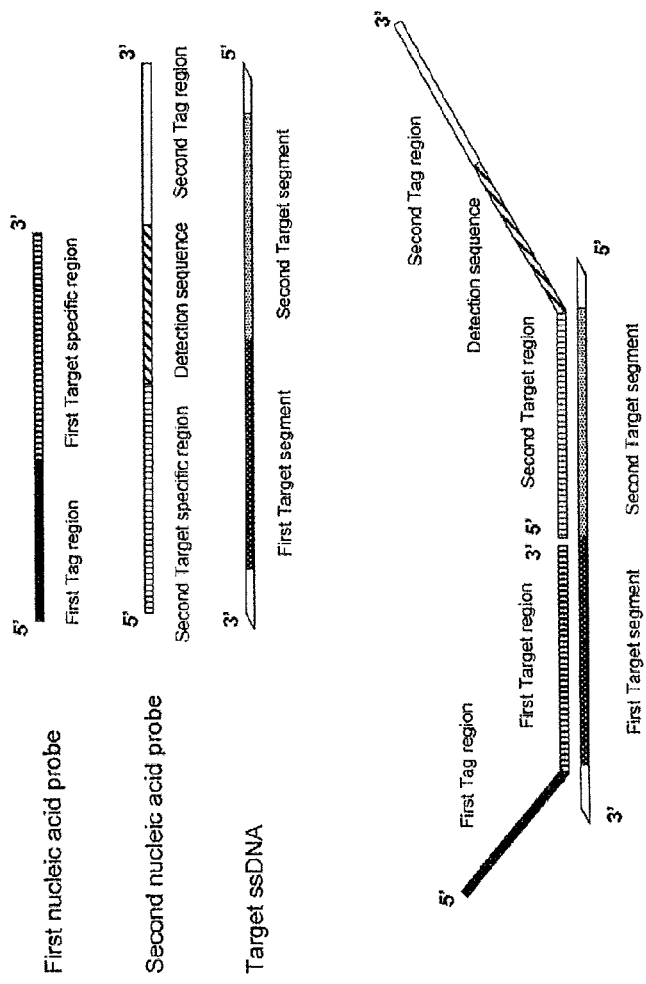
FIGURE 2. Probe sets and Target DNA

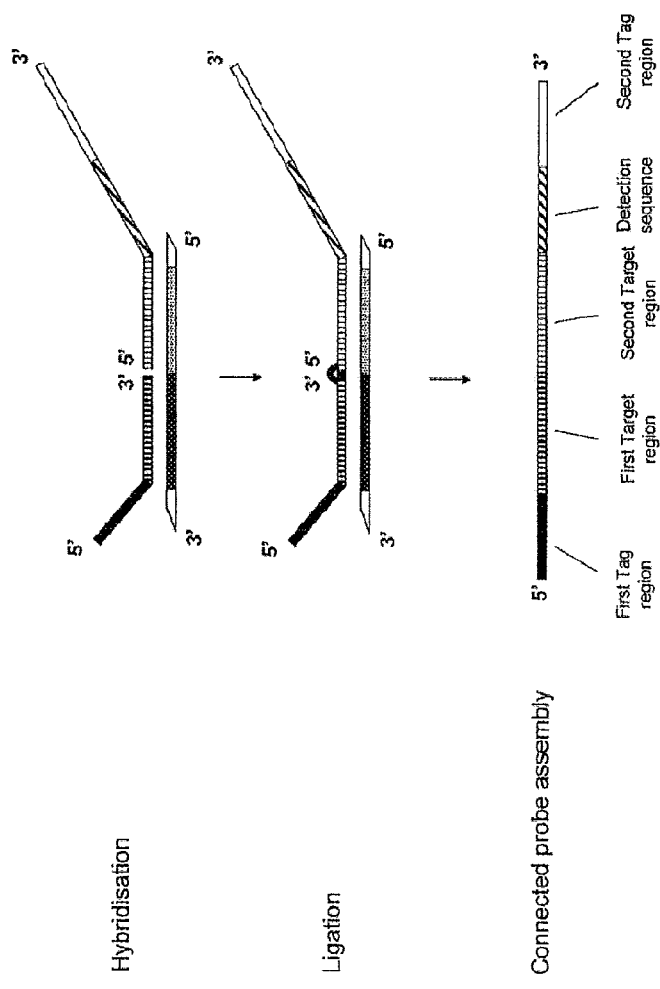
FIGURE 3. Formation of a connected probe assembly by a ligation step

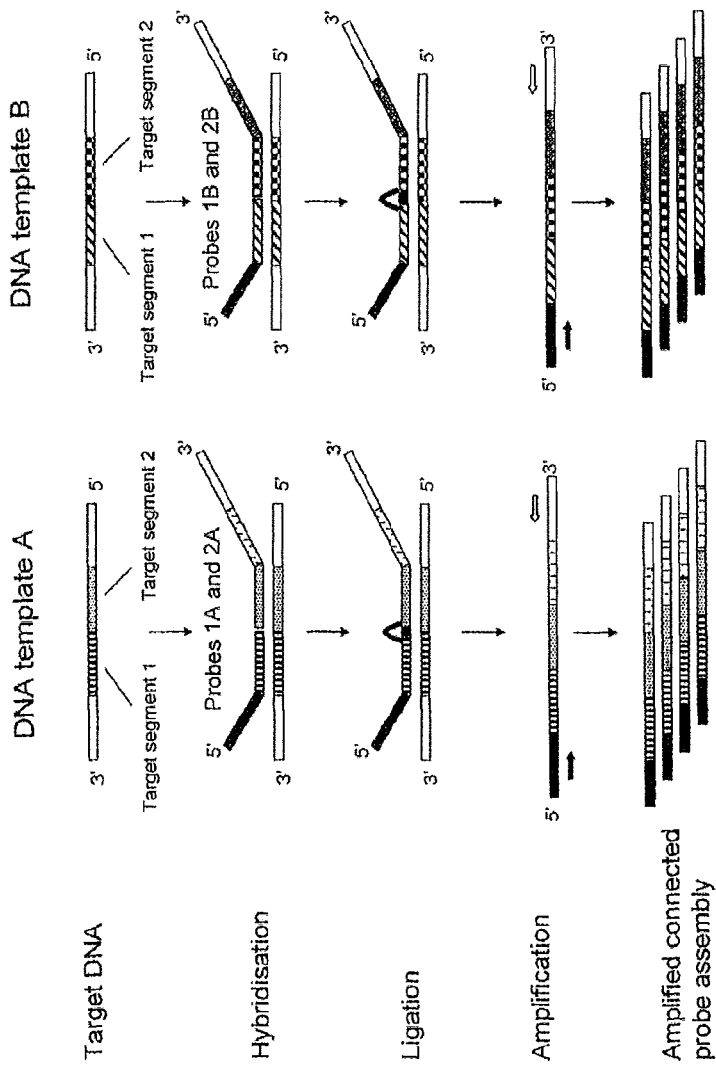
FIGURE 4 Overview of the formation of amplicons of a connected probe assembly starting from 2 distinct DNA templates A and B

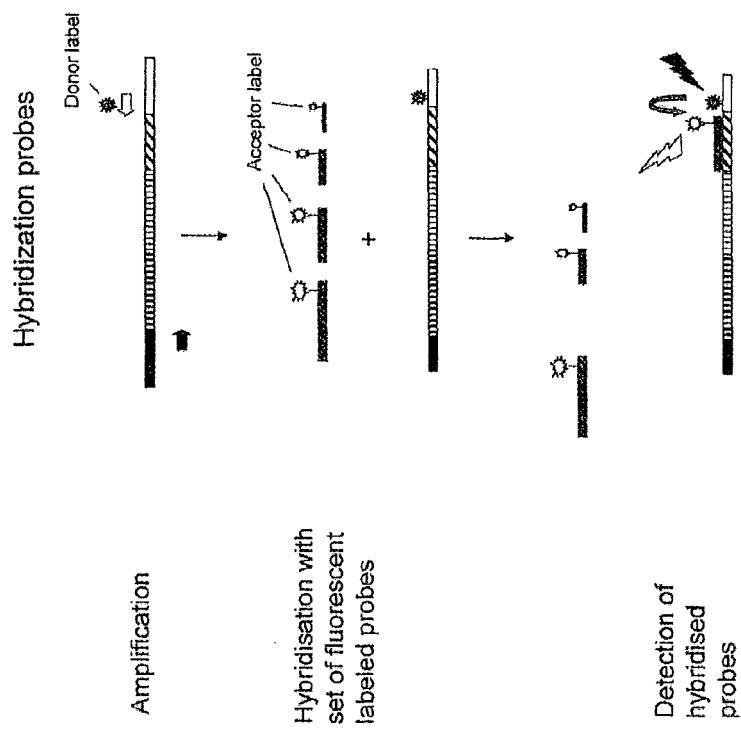
FIGURE 5. Real time PCR

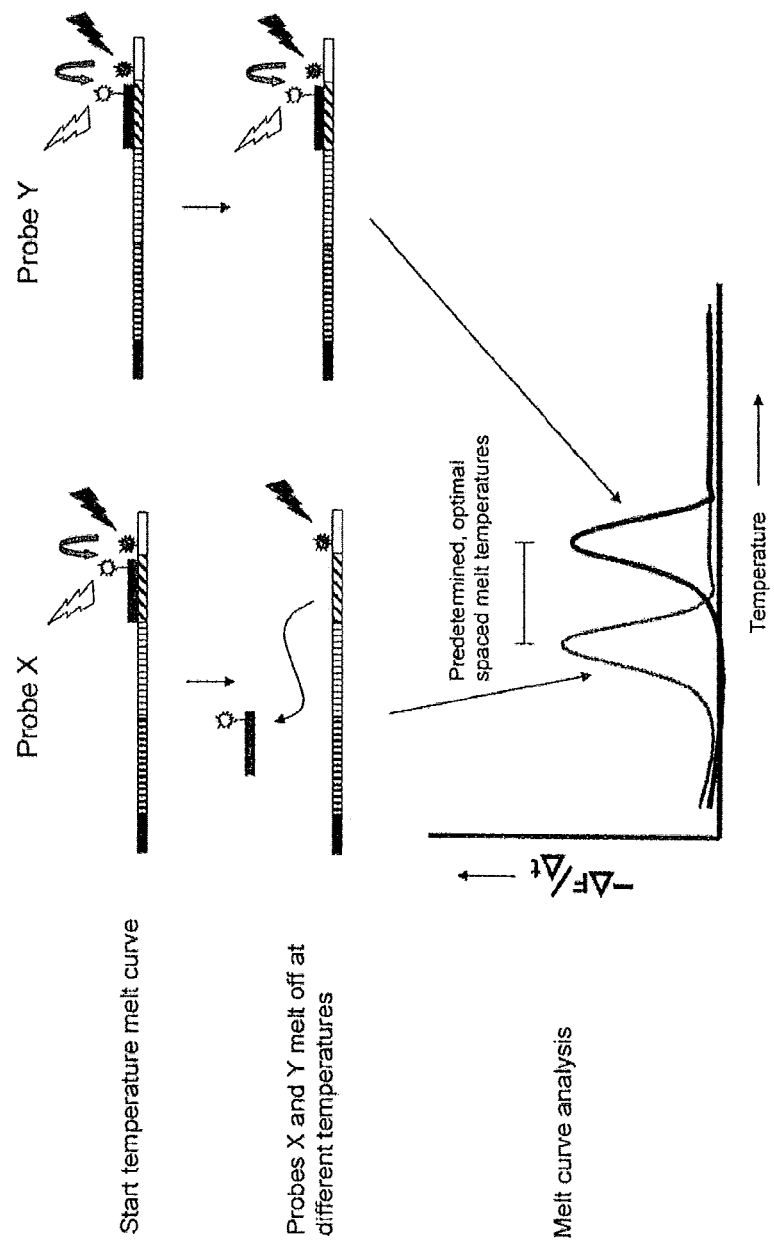

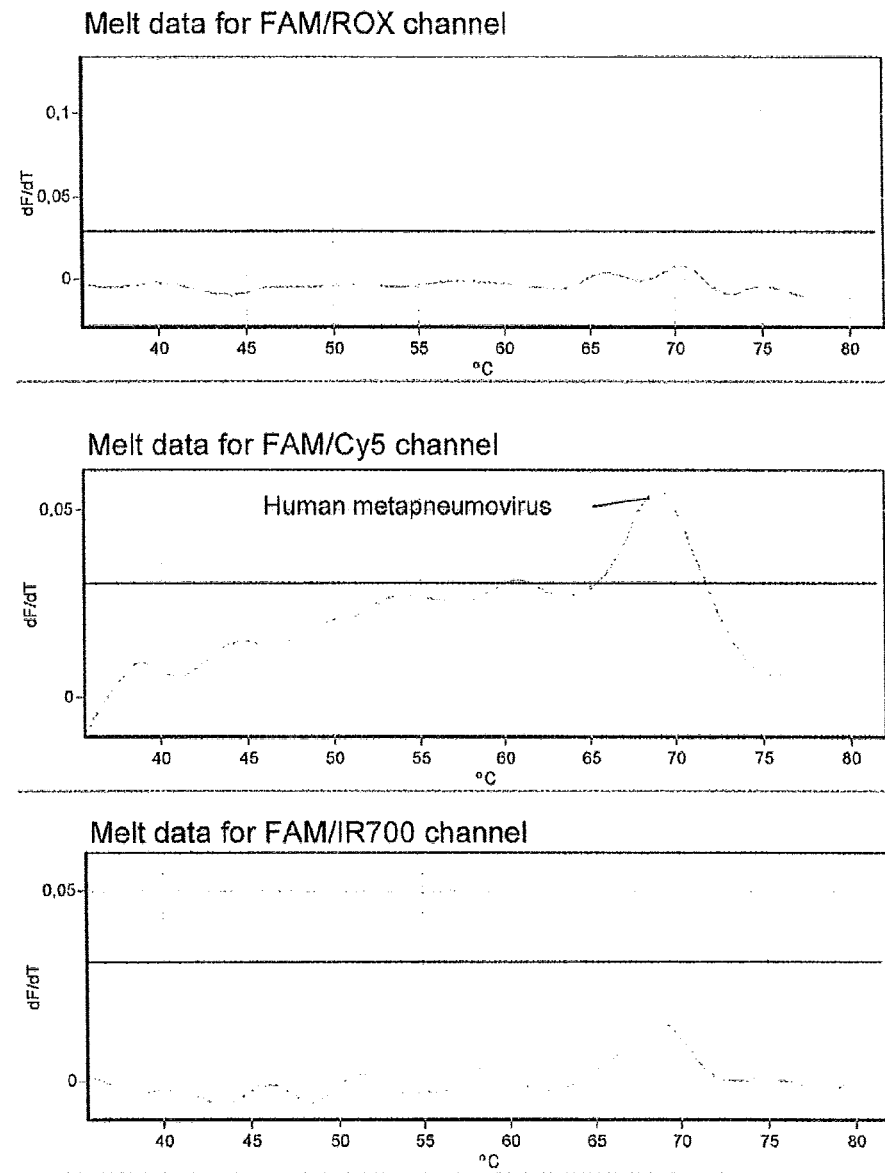
Figure 7. Melt curve analysis of three channels of a clinical sample containing human metapneumovirus. The human metapneumovirus detection probe is labeled with Cy5 and has a theoretical melting temperature of 70°C.

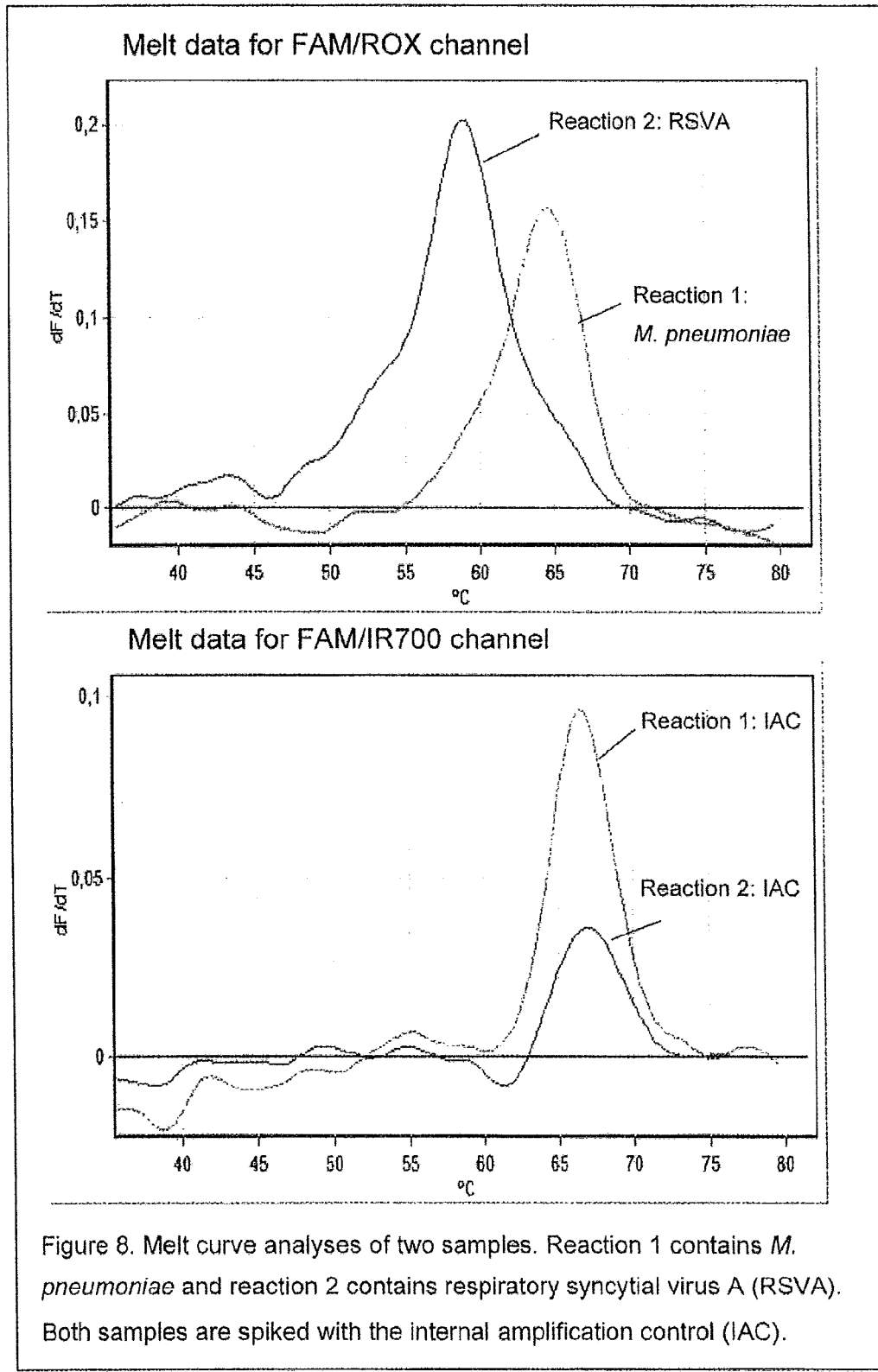
Figure 8. Melt curve analyses of two samples. Reaction 1 contains *M. pneumoniae* and reaction 2 contains respiratory syncytial virus A (RSVA). Both samples are spiked with the internal amplification control (IAC).

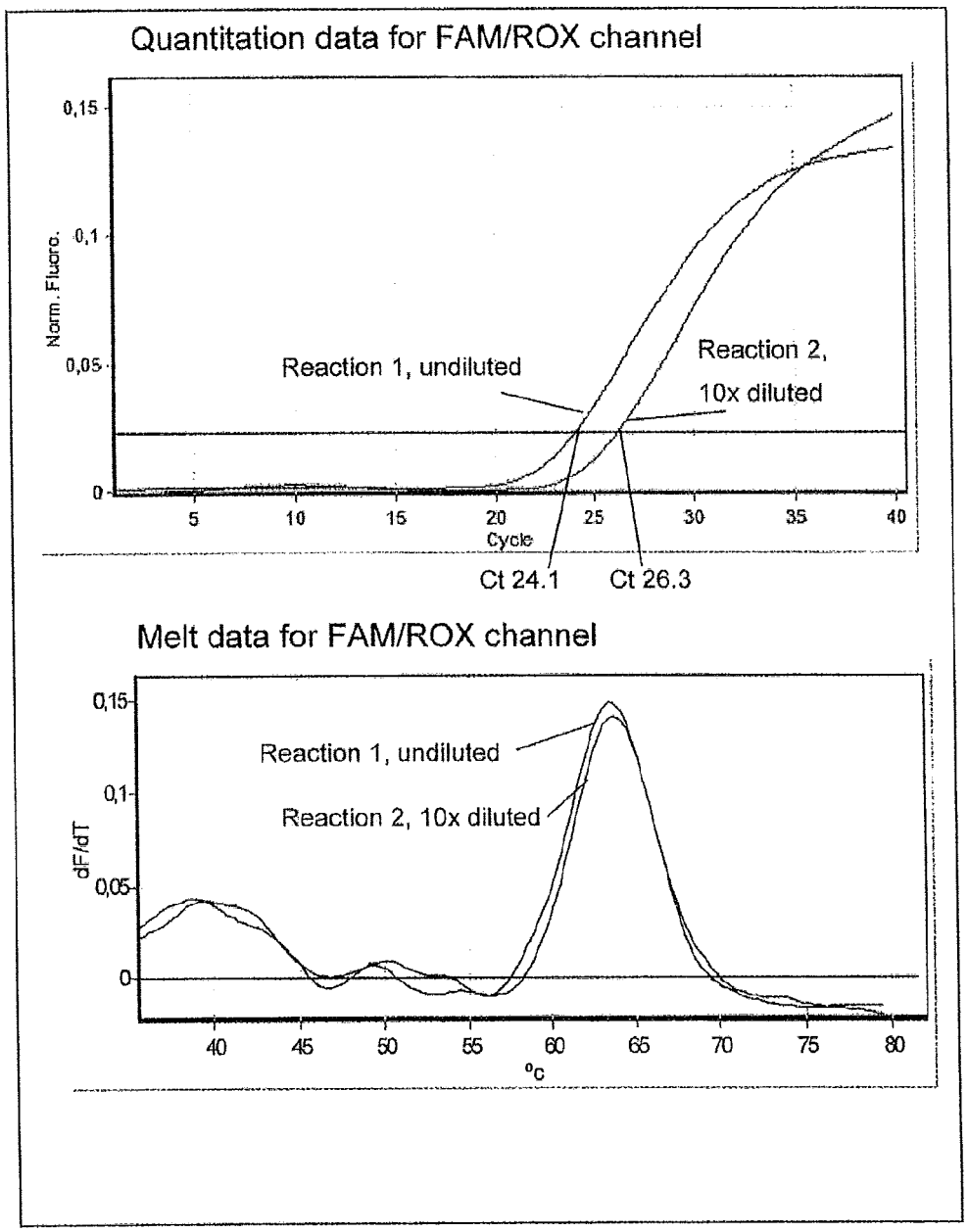
Figure 9. Quantitation data and melt data of a sample containing *M. pneumoniae*. Reaction 1 contains the undiluted sample, reaction 2 contains the 10x diluted sample.

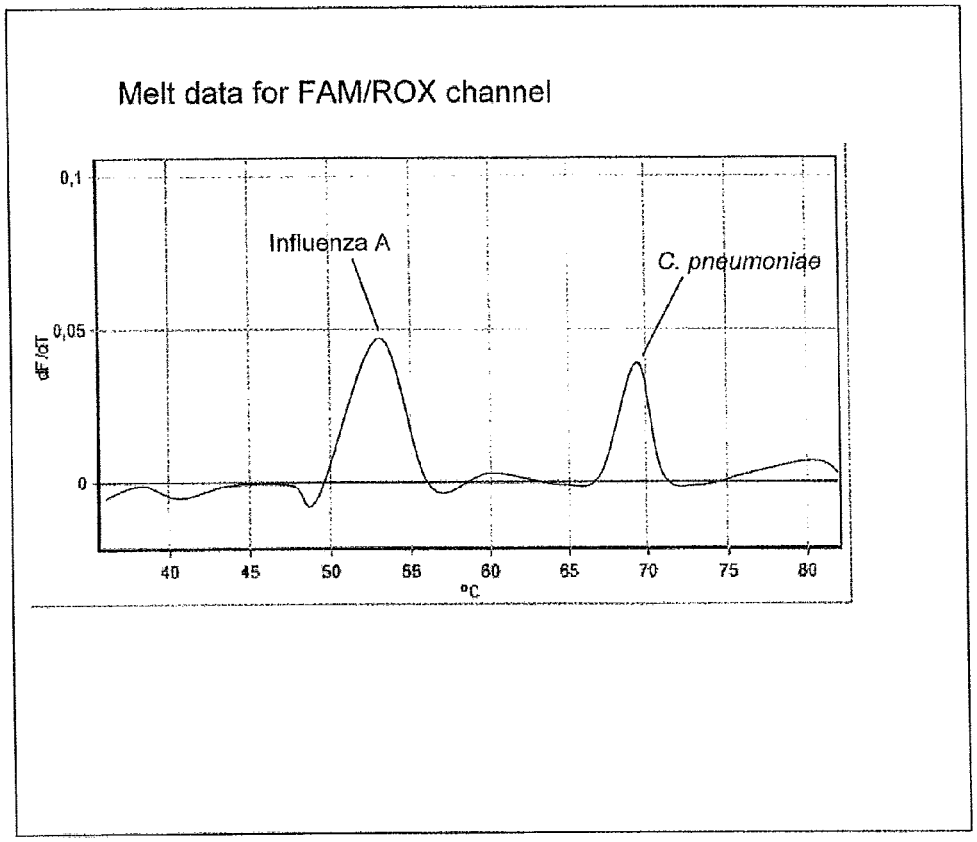
Figure 10. Impression of a melt curve analysis of a sample containing a co-infection of Influenza A virus and C. pneumoniae.

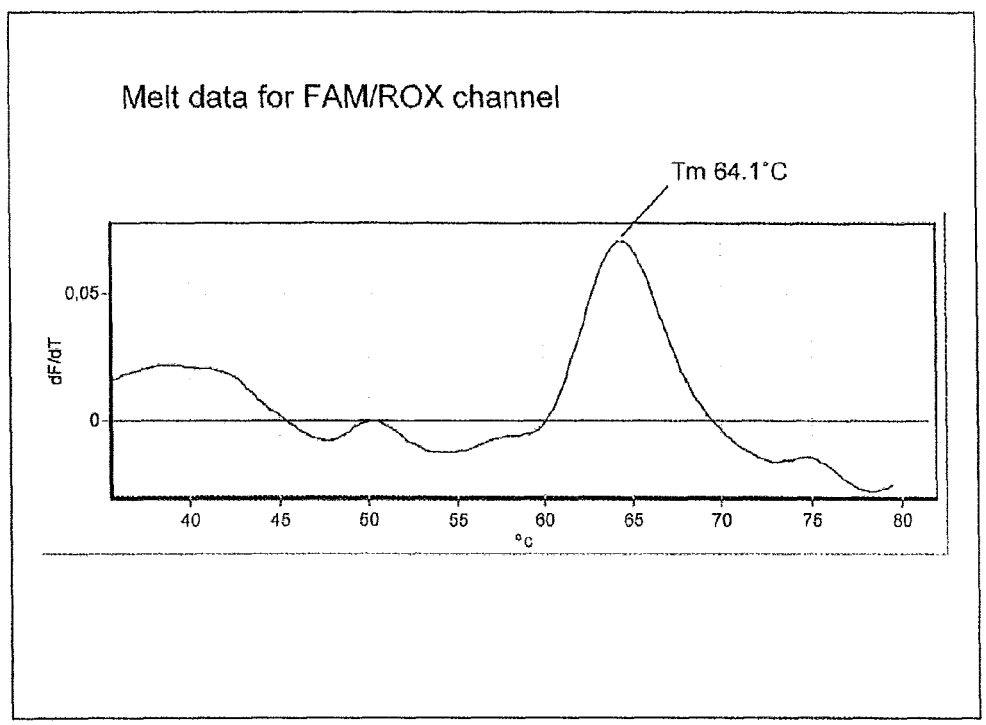
Figure 11. Melt curve analysis of a OneTube reaction plus detection in a single reaction vessel from a sample containing M. pneumoniae.

METHOD FOR THE SIMULTANEOUS DETECTION OF MULTIPLE NUCLEIC ACID SEQUENCES IN A SAMPLE

This application is the U.S. national phase of International Application No. PCT/EP2008/059050 filed 10 Jul. 2008, which designated the U.S. and claims priority to EP Application No. 07112219.6 filed 11 Jul. 2007, the entire contents of each of which are hereby incorporated by reference.

FIELD OF THE INVENTION

The invention relates to the technical field of detecting multiple nucleic acid sequences in a sample, such as the detection of pathogenic organisms in clinical samples. More specifically, the invention relates to the field of detecting an infection caused by a pathogenic organism such as a virus or a bacterium in a clinical specimen by means of amplifying and detecting specific nucleic acid sequences from said pathogenic organism.

BACKGROUND OF THE INVENTION

Infectious agents such as micro-organisms are typically detected by culturing clinical samples under conditions favourable for the growth of such micro-organisms and monitoring that growth by a number of different techniques including microscopy and detection of more or less specific metabolites of the organisms.

Nucleic acid amplification tests to identify pathogens rapidly and reliably have been implemented in the microbiology laboratory during the last decade. Nucleic acid amplification tests can be used to detect the presence of micro-organisms directly in clinical specimens without culturing.

Initially, identification was accomplished by amplification of a target nucleic acid sequence and detecting of the resulting DNA by visualisation using gel electrophoresis and DNA-binding fluorescent dyes.

Nucleic acid amplification tests revolutionized the world of clinical diagnosis in that they provided an increase in sensitivity and speed of an order of several magnitudes as compared to the classical culture assays.

In general, nucleic acid amplification tests consist of a target specific nucleic acid amplification step and a more or less generic detection step. Herein below follows a brief summary of available amplification techniques and detection platforms.

PCR is currently still the first choice to amplify target sequences and the ability to amplify a wide range of pathogens is dependent on generic, random or multiplex amplification technologies.

In generic PCR tests, only one or two primers pairs are necessary to amplify a target sequence from a range of related pathogens. Regions of conserved nucleotide sequences are required and in general degenerate primer pairs are used.

Several random amplification technologies exist, making use of either random octamers or primers that contain a random 5-8 nucleotide extension at its 3'-end and a defined sequence at its 5'-end. Random amplification is performed in combination with Taq polymerase or isothermal polymerase-based amplification enzymes such as Klenow DNA polymerase or φ29 DNA polymerase.

Multiplex PCR involves the combination of several primers pairs targeting different sequences in one amplification reaction. Multiplex PCRs require careful optimization to make them comparably sensitive and specific as single pair amplification reactions.

Multiplex Ligation-dependent Probe Amplification (MLPA) technology (Schouten et al; WO 01/61033, Schouten et al., Nucl. Acids Res. 2002, vol 30 No 12; e57) is a multiplex PCR method capable of amplifying different targets simultaneously. In MLPA two oligonucleotides that hybridise immediately adjacent to each other on target DNA are added in the same reaction. One of the oligonucleotides is synthetic and has a size of 40-60 nucleotides (nt) whereas the other oligonucleotide has a size ranging from 100 up to 400 nt and requires a cloning step in an M13 vector to finally generate single stranded probe DNA. MLPA consists of three steps: first an annealing step to hybridise the probes to their target region, secondly a ligation step to covalently link the two probes together and thirdly the final PCR to get an exponential amplification of the target regions using only two universal primers.

Currently, target specific multiplex PCR amplification is the standard method for pathogen detection assays.

Because of the extreme sensitivity of nucleic acid amplification tests, care must be taken to avoid contamination in these tests. Detection of amplified nucleic acids was originally performed by size determination using gel electrophoresis and intercalating DNA dyes. A first step in minimizing contamination was taken when the amplification and detection steps were combined into one step. As a result, post-amplification handling steps were eliminated, thereby adding to the reliability of the assay. Such assays are often referred to as a closed system. Closed system amplification technologies such as real time PCR (Ratcliff et al. Curr Issues Mol. Biol. 2007, 9(2): 87-102) and NASBA (Loens et al., J Clin Microbiol. 2006, 44(4); 1241-1244) and LAMP (Saito R et al., J Med. Microbiol. 2005, 54; 1037-41) have been developed and use intercalating fluorescent dyes or fluorescent labelled probes. The isothermal LAMP technology allows real time detection by spectrophotometric analysis using a real-time turbidimeter. Currently, most of these assays are organism-specific and useful only when a particular pathogen is suspected. This limits the scope of these assays considerably.

However, clinical symptoms are only rarely attributable to a single pathogen. Hence, there is a need in the art for assays that allow the simultaneous identification and differentiation of multiple agents. Such multi-parameter assays enable the clinician to come to a faster and better therapy and contribute to improved clinical management and public health.

For this reason technologies have been developed for the purpose of testing simultaneously for more than one organism. One of such technologies is multiplex real time PCR. At present, however, only five colour oligo-probe multiplexing is possible of which one colour is ideally set aside for an internal control to monitor inhibition and perhaps even acts as a co-amplified competitor (Molenkamp et al. J. Virol Methods, 2007, 141: 205-211). This considerably limits the amount of pathogens that may be tested simultaneously.

An example of an area where it is particularly desirable to have a quick, reliable and specific multiplex assay for several pathogens at once, is the area of respiratory tract infections.

Acute respiratory tract infection is the most widespread type of acute infection in adults and children. The number of pathogens involved is numerous. Respiratory tract infections (RTI) are commonly divided into upper respiratory tract infections (URTI) and lower respiratory tract infections (LRTI). The URTI include rhinorrhea, conjunctivitis, pharyngitis, otis media and sinusitis and LRTI include *pneumoniae*, brochiolitis and bronchitis. Both viruses and bacteria cause acute RTI, and the number of causative agents is large as well as diverse.

Non-typical viruses and bacteria involved in RTI include influenza virus A and B (InfA and B), parainfluenza virus 1, 2, 3 and 4 (Ply-1, -2, -3 and 4), respiratory syncytial virus A and B (RSVA and B), rhinovirus, coronavirus 229E, OC43 and NL63 (Cor-229E, -OC43 and NL63), severe acute respiratory syndrome coronavirus (SARS-CoV), human metapneumovirus (hMPV), adenovirus, *Mycoplasma pneumoniae, Chlamydia pneumoniae, Legionella pneumophila* and *Bordetella pertussis*. Many of these infections are indistinguishable by clinical features alone and require rapid laboratory tests for optimal patient management and infection control.

Viral culture is still the gold standard for laboratory diagnosis of respiratory viruses. However, viral culture is relatively slow and therefore routine diagnosis is sub optimal. Although rapid antigen detection tests are available for some of these viruses, these tests have shown to be less sensitive and less specific than viral culturing. Currently, there is a desperate need for a sensitive and specific method for the simultaneous detection of respiratory viruses in a multiplex format. It would be very advantageous to be able to detect two or more targets in a single reaction as this would provide distinct advantages in clinical diagnostics. It would simplify the assay, increase the throughput, minimize the consumption of clinical specimen and in particular multiplex assays would be more cost-effective than monoplex assays.

To differentially detect respiratory viruses in clinical specimens the following detection platforms have been used:

(i) Gel Electrophoresis.

Using agarose gel electrophoresis as detection device, several nested multiplex reverse transcriptase (RT)-PCR assays have been developed using three or four primer pairs. Osiowy et al., (J. Clin. Microbiol. 1998, 36; 3149-3154) used five primers pairs that amplified RNA from respiratory syncytial virus A and B, parainfluenza virus 1, 2 and 3 and adenovirus types 1 to 7. The PCR products varied in size from 84 up to 348 base pairs. Compared to direct immunofluorescence (DIF) assays or indirect immunofluorescence (IIF) assays a sensitivity value of 91% and a specificity value of 87% was obtained for this multiplex RT-PCR approach.

Coiras et al. (J. Med. Virology, 2004, 72; 484-495) using the same approach, were able to simultaneously detect 14 respiratory viruses in two multiplex RT nested PCR assays. They included coronavirus 229E and OC43, rhinovirus, enterovirus, parainfluenza virus 4 and an internal control but omitted adenovirus 1 to 7. The assay was evaluated on nose and throat swaps and nasopharyngeal aspirates from infants below two years of age. It appeared that the multiplex assay was more sensitive than conventional viral culture and immunofluorescence assays, with the advantage that all viruses can be tested at the same time and with a single technique. In addition, in 9.5% of the samples a double infection was found.

Erdman et al. (J. Clin. Microbiol. 2003, 41; 4298-4303) recently developed a RT-PCR assay against 6 common respiratory viruses based on automated fluorescent capillary electrophoresis and Genescan software for detection of respiratory syncytial virus A and B, parainfluenza virus 1, 2 and 3 and influenza virus A and B. An one-step RT-PCR reaction was performed using primers of which the positive strand primer of each primer set was 5' end labelled with the fluorescent dye 6-carboxyfluorescein (6-FAM). Overall, this RT-PCR assay was positive in 92% of the samples that were also positive by culture or DIF staining.

The above references are examples of techniques wherein a large number of samples is analysed using gel-electrophoresis. Disadvantages of gel electrophoresis as a detection technique are that it is laborious and time consuming and therefore rather costly. Furthermore, the risk of cross contamination is enlarged as each sample has to be opened after the PCR for analysis.

(ii) Secondary Enzyme Hybridisation.

In this approach multiplex PCR assays are combined with an enzyme-linked immunosorbent assay (ELISA).

Detection of the multiplex PCR products is performed by microwell hybridisation analysis in streptavidin-coated wells of a microtiter plate. Biotinylated capture probes specific for the amplified target sequences are added and a peroxidase labelled hybridisation reaction is performed. Subsequently, the optical density is measured by a reader/spectrophotometer. Samples are classified as PCR positive or negative depending on the cut-off optical density value.

Multiplex RT-PCR enzyme hybridisation assays for rapid identification of seven or nine micro-organisms causing a respiratory tract infection have been developed and validated in comparison to the gold standard. The commercially available Hexaplex assay (Prodesse, Inc., Milwaukee, Wis.) (Fan et al, Clin. Infect. Dis. 1998, 26; 1397-1402, Kehl et al., J. Clin. Microbiol. 2001, 39; 1696-1701 and Liolios et al., J. Clin. Microbiol. 2001, 39; 2779-2783) is directed against parainfluenza virus 1, 2 and 3, respiratory syncytial virus A and B and influenza virus A and B whereas the nineplex assay contained the same RNA viruses minus parainfluenza 2 and respiratory syncytial virus A and B were combined in one primer pair but including enterovirus, adenovirus and two bacteria *Mycoplasma pneumoniae* and *Chlamydia pneumoniae* (Grondahl et al., J. Clin. Microbiol. 1997, 37; 1-7 and Puppe et al., J. Clin. Virol. 2003, 30; 165-174). The analytical sensitivity of the Hexaplex assay has been shown to be 100-140 copies/ml depending on the virus, whereas the nineplex assay was less sensitive compared to culture for respiratory syncytial virus and parainfluenza virus 1 and more sensitive for parainfluenza virus 3, influenza virus A and B, adenovirus and enterovirus. The analytical sensitivity was measured on serial dilutions of viral culture supernatants. The sensitivity and specificity of the nineplex and hexaplex on clinical specimens varied between the RNA viruses and was found to be between 86%-100% for sensitivity and 80%-100% for specificity. Both assays were compared with monoplex RT-PCR ELISA and other monoplex RT-PCR tests and were approximately of the same quality. Although the ELISA based assays allow highly multiplex analyses, they posses the same disadvantages as the gel electrophoresis based assays. The assays are laborious and time consuming and the reaction vessel has to be opened after PCR, thereby increasing the risk of cross contamination.

(iii) Measuring Emission Using Different Fluorescent Dyes.

Fluorescence reporter systems such as real time PCR have been introduced in the diagnostic laboratory recently. Real Time PCR combines DNA amplification with detection of the products in a single tube. Detection is based on changes in fluorescence proportional to the increase in product. Real Time PCR capacity to simultaneously detect multiple targets is limited to the number of fluorescent emission peaks that can be unequivocally resolved. At present, only four colour oligoprobe multiplexing is possible of which one colour is ideally set aside for an internal control to monitor inhibition and perhaps even acts as a co-amplified competitor.

Many monoplex or duplex real-time PCR assays against respiratory pathogens have been developed either being home brew based (van Elden et al., J. Clin. Microbiol. 2001, 39; 196-200, Hu et al, J. Clin. Microbiol. 2003, 41; 149-154) or commercially available assays (Prodesse, Inc., Milwaukee, Wis.). One of the first multiplex real-time PCR assays directed against respiratory viruses was developed by Templeton et al. (J. Clin. Microbiol. 2004, 42; 1564-1569). A real-time multiplex PCR assay was developed for the detection of 7 respiratory RNA viruses (influenza virus A and B, respiratory syncytial virus, parainfluenza virus 1, 2, 3 and 4) in a two-tube multiplex reaction. Each assay was initially set up as a monoplex assay and then combined in two multiplex assays: one comprises influenza virus A and B and respiratory syncytial virus whereas as the other one comprises parainfluenza virus 1, 2, 3 and 4 with both assays having the same PCR protocol so they could be run in parallel. No non-specific reactions or any inter-assay cross-amplification was observed and only the correct virus was amplified by the two multiplex reactions. Clinical evaluation was performed by viral culture and confirmed by IF and multiplex PCR on the same samples. Viral culture resulted in 19% positive samples whereas multiplex resulted in 24% positives. The multiplex PCR-positive specimens included all the samples that were positive by viral culture and additional ones. The additional ones were tested by a second PCR-assay and it could be shown that that these samples were true positives.

For simultaneous detection of 12 respiratory RNA viruses by real-time PCR, Gunson et al. (J. Clin. Virol. 2005, 33; 341-344) developed four triplex reactions: (i) influenza virus A and B and human metapneumovirus, (ii) respiratory syncytial virus A and B and rhinovirus, (iii) parainfluenza virus 1, 2 and 3 and (iv) coronavirus 229E, OC43 and NL63. These 4 assays cover almost the complete set of respiratory RNA viruses and implementation of these assays was said to improve patient management, infections control procedures and the effectiveness of surveillance systems. The real time PCR assays allow analysis without any post PCR handling of the sample. This diminishes the risk of cross contamination and requires no extra handling time. However, the complexity of the current assays is limited to a maximum of four probes per reaction. Moreover, complex analyses require more reactions thereby increasing the costs.

(iv) Microarrays Consisting of Oligonucleotides or PCR Amplicons Immobilized on a Solid Surface.

Microarrays for diagnostic purposes require either (a) genome specific probes to capture the unknown target sequences or (b) generic zipcodes present in the amplified target sequence and thereby reveal the presence of that pathogen in a clinical specimen. Hybridisation between the bound probe and target sequence in the sample is revealed by scanning or imaging the array surface.

DNA microarrays offer the possibility for highly parallel viral screening to simultaneously detect hundreds of viruses. Related viral serotypes could be distinguished by the unique pattern of hybridisation generated by each virus. High density arrays are able to discriminate between ten thousand different targets whereas low density arrays of up to a few hundred targets are more appropriate in clinical diagnostics. The first array for use in diagnostic virology was constructed by Wang at al. (Proc. Natl. Acad. Sci. USA 99; 15678-15692). They initially constructed a microarray of 1600 unique 70-mer oligonucleotide probes designed from about 140 viral genome sequences of which the respiratory tract pathogens were of major concern. The viral RNA was amplified using a randomly labelled PCR procedure and the array was validated with nasal lavage specimens from patients with common colds. The array detected respiratory pathogens containing as few as 100 infectious particles. The data were confirmed with RT-PCR using specific PCR primers. Cross hybridisation was only observed to its close viral relatives.

Low density arrays have been constructed for detection, typing and sub-typing of Influenza (Kessler et al., J. Clin. Microbiol. 2004, 42; 2173-2185) and acute respiratory disease-associated adeno viruses (Lin et al., J. Clin Microbiol. 2005, 42; 3232-3239). The Influenza chip was shown to detect as few as $1 \times 10^2$ to $5 \times 10^2$ influenza virus particles whereas the sensitivity of the adeno microarray was $10^3$ genomic copies when clinical samples were analysed directly. Multiplex as well as random amplification procedures were used.

A very new development in respiratory tract pathogen identification is the use of re-sequencing microarrays (Lin et al., Genome Res., 2006, 16:527-535, and Wang et al, Bioinformatics 2006 22(19):2413-2420; doi:10.1093/bioinformatics/btl396). The exponentially increasing availability of microbial sequences makes it possible to use direct sequencing for routine pathogen diagnostics. However, this requires that pathogen sequence information be rapidly obtained. Resequencing microarrays use tiled sets of $10^5$ to $10^6$ probes of either 25-mers or 29-mers, containing one perfectly matched and three mismatched probes per base for both strands of target genes. A custom designed Affymetrix resequencing Respiratory Pathogen Microarray (RPM v.1) has been disclosed. This RPM v.1 array harbours 14 viral and bacterial species. A random amplification protocol was used and in both studies identification not only at the species level but also at the strain level was obtained. This is of particular interest for surveillance of epidemic outbreaks. The development of a second RPM chip (v.2) has already been initiated including 54 bacterial and viral species. However, the sensitivity and assay speed has to be improved to provide a diagnostic platform for pathogen detection.

The immediate precursor of a DNA array suitable in clinical diagnostics was the reverse hybridisation line probe or blot. Line probe/blot assays have been described for mutation detections and for genotyping and are also commercially available (line probe assay (LiPA) from Innogenetics, Belgium). Generally, a generic amplification technology is used but up to now no studies have been published of line probe blots against respiratory viral pathogens. The microarray based assays allow highly complex analyses. However, they require specialized equipment and extensive post PCR handling.

(v) Beads or Microspheres Systems

In these products, detection is performed by a flow cytometer. In such a system microspheres are internally dyed with two spectrally distinct fluorochromes. Using precise amounts of each of these fluorochromes, an array is created consisting of 100 different microspheres sets with specific spectral properties. Due to this different spectral property, microspheres can be combined, allowing up to 100 different targets to be measured simultaneously in a single reaction. For nucleic acid detection using microspheres, direct hybridisation of a labelled PCR amplified target DNA to microspheres bearing oligonucleotide capture probes products specific for each target sequence are used. Detection is performed by two lasers, one to identify the distinct bead set and the other one to determine the specific target sequence.

Microsphere-based suspension array technologies, such as the Luminex® xMAP™ system, offer a new platform for high throughput multiplex nucleic acid testing. Compared to planar microarrays, they have the benefits of faster hybridisation kinetics and more flexibility in array preparation. Recently, a novel microsphere-based universal array platform, called the Tag-It™ platform has been developed and used for detection and differentiation of 19 respiratory viruses. The Tag-It™ array platform features universal, minimally cross-hybridizing tags for capturing the reaction products by hybridisation onto complementary anti-tag coupled microspheres. The respiratory viral panel on the Luminex platform was developed by TM Biosciences (Toronto, Canada) and validated on nasopharyngeal swabs and aspirates. An overall sensitivity of 96.1% was obtained and data were confirmed by monoplex PCR and DFA. In addition 12 double (out of 294 specimen samples) infections were detected. As with the microarray based assays, these assays allow highly complex analyses but require specialized equipment and extensive post PCR handling.

(vi) Mass Spectrometry Systems

These are assays wherein tags are released by UV irradiation and subsequently analyzed by a mass spectrometer. Oligonucleotide primers, designed against conserved regions of the pathogen, are synthesized with a 5' C6 spacer and aminohexyl modification and covalently conjugated by a photocleavable link to (Masscode) tags. A library of 64 different tags has been established. Forward and reverse primers in individual primer sets are labelled with distinct molecular tags. Amplification of a particular pathogen target results in a dual signal in a mass spectrometer that allows assessment of specificity.

Mass spectrometry is a homogeneous solution assay format that allows for simultaneous detection of multiple nucleic acid sequences in a single reaction thereby reducing time, labour and cost as compared to single-reaction-based detection platforms. A new class of molecular labels, called cleavable mass spectrometry tags (CMSTs) has been developed for simultaneous data acquisition. One application of CMST technology is termed Masscode (Qiagen, Hilden, Germany) and is used for differential detections of respiratory pathogens. The general structure of CMSTs is highly modular and includes a photolabile linker, a mass spectrometry sensitivity enhancer and a variable mass unit all connected through a scaffold constructed around a central lysine residue. CMSTs are attached to the 5'-end of the oligonucleotide of the PCR primer through a photo-cleavable linker. The combination of the enhancer and the variable mass unit specify the final mass of each individual CMST. Currently, a library of 64 distinct Masscode tags has been developed and a variety of mass spectrometry ionization methods can be applied. A great advantage of detection by mass spectrometry is the speed. Analysis takes only a few seconds.

Briese et al. (Emerg. Infect. Dis., 2005, 11; 310-313) developed a diagnostic assay comprising of 30 gene targets that represented 22 respiratory pathogens. Nucleic acid from banked sputum, nasal swabs and pulmonary washes was tested and compared to virus isolation and conventional nested RT-PCR. Consistent results were obtained. The detection threshold was between 100-500 copies per sample. Mass spectrometry is a very fast technique enabling highly complex analyses. However, this application requires specialized and expensive hardware which, at the moment, is not common on a standard microbiology laboratory.

The above described multiparameter approaches to identify and differentiate the causative agents of a RTI are a great step forward but still have limitations. They take either too much time (>10 hours), require a lot of hands-on time, have a limited multi-parameter character and/or need expensive equipment or large set-up costs to perform the tests.

SUMMARY OF THE INVENTION

Herein we describe a new multi-parameter approach to detect and differentiate various pathogens in a clinical sample.

The invention is in the technical field of detecting nucleic acid sequences in a sample, such as the detection of pathogenic organisms in clinical samples. More specifically, the invention relates to the field of detecting an infection caused by a pathogenic organism such as a virus or a bacterium in a clinical specimen by means of amplifying and detecting specific nucleic acid sequences from said pathogenic organism. It provides a multiplex assay with the possibility to determine about 30 different target nucleic acid sequences in a single one-tube assay combined with real-time probe detection.

The invention relates to a method capable of simultaneously detecting a plurality of different target DNA templates in a sample, each DNA template comprising a first target segment and a second target segment, the combination of both target segments being specific for a particular target DNA template, wherein the first and second target-specific segments are essentially adjacent to one another and wherein the first target segment is located 3' from the second target segment, said method comprising the steps of:

a) an optional reverse transcription and/or pre-amplification step,
b) bringing at least one DNA template into contact with a plurality of different probe sets, each probe set being specific for one target DNA template and allowing the at least one DNA template to hybridise with a probe set specific for the at least one DNA template,
c) forming a connected probe assembly comprising the specific probe set,
d) amplifying the connected probe assembly to obtain at least one amplicon,
e) detecting the presence of the at least one amplicon by performing a real-time melting curve analysis, wherein a donor or acceptor label is incorporated in the first or second tag region, essentially adjacent to the detection region and wherein step e) is performed by providing a plurality of detection probes comprising
at least one fluorescent donor label or at least one acceptor label complementary to the label incorporated in the first or second tag region,
a nucleic acid region specifically hybridisable to said detection sequence
allowing the at least one amplicon to hybridise with the plurality of detection probes
monitoring hybridisation of the labelled detection probe at least one pre-selected temperature by measuring the fluorescence of the acceptor label, wherein said hybridisation of the labelled detection probe is indicative for the presence of a target DNA template in the sample.

Also, the invention relates to a kit for performing such a method comprising a) A plurality of different probe sets
b) A source of a DNA ligase activity
c) A source of a DNA polymerase activity
d) At least one primer comprising at least one donor label
e) A plurality of detection probes comprising at least one fluorescent label,
f) Instructions for performing the method.

LEGEND TO THE FIGURES

FIG. 1 shows a schematic overview of the optional reverse transcription and pre-amplification step of the method according to the invention.

FIG. 2 shows a schematic overview of the probe sets used in the method according to the invention and their hybridisation to the first and second target segments of the at least one DNA template.

FIG. 3 shows a schematic overview of a step wherein the probe sets are incorporated into a connected probe assembly. As a preferred example of such a step it is shown how the hybridisation probes are connected by the action of a ligase.

FIG. 4 provides a schematic overview of the formation of amplicons of a connected probe assembly starting from 2 distinct DNA templates A and B.

FIG. 5 shows a schematic overview of real time PCR detection on a connected probe assembly. Exemplified herein is the detection using hybridisation probes.

FIG. 6 shows a schematic overview of a melting curve analysis employing two different probes X and Y with different melting temperatures. This results in distinguishable signals in the melting curve analysis.

FIG. 7 shows a melt curve analysis of three channels of a clinical sample containing human metapneumovirus. The human metapneumovirus detection probe is labelled with Cy5 and has a theoretical melting temperature of 70° C.

FIG. 8 shows a melt curve analysis of two samples. Sample 1 contains *Mycoplasma pneumoniae* and sample 2 contains respiratory syncytial virus A. Both samples are spiked with the internal amplification control.

FIG. 9 shows quantitative data of a sample containing *Mycoplasma pneumoniae*. Reaction 1 contains the undiluted sample, reaction 2 contains the 10× diluted sample.

FIG. 10 shows an impression of a melt curve analysis of a sample containing a co-infection of influenza virus A virus and *Chlamydia pneumoniae*.

FIG. 11 shows a melt curve analysis of a OneTube reaction from a sample containing *Mycoplasma pneumoniae*.

DETAILED DESCRIPTION OF THE INVENTION

In one aspect, the invention relates to a method capable of simultaneously detecting a plurality of different target DNA templates in a sample, each DNA template comprising a first target segment and a second target segment, the combination of both target segments being specific for a particular target DNA template, wherein the first and second target-specific segments are essentially adjacent to one another and wherein the first target segment is located 3' from the second target segment, said method comprising the steps of:
 a) an optional reverse transcription and/or pre-amplification step,
 b) bringing at least one DNA template into contact with a plurality of different probe sets, each probe set being specific for one target DNA template and allowing the at least one DNA template to hybridise with a probe set specific for the at least one DNA template,
 c) forming a connected probe assembly comprising the specific probe set,
 d) amplifying the connected probe assembly to obtain at least one amplicon,
 e) detecting the presence of the at least one amplicon by performing a real-time melting curve analysis Such a method has been disclosed in EP1130113A1. Therein the detection of an amplicon obtained by multiplex ligation dependent amplification (MLDA) is described by performing a real time melting curve analysis. In that kind of analysis, a number of different stuffer fragments are provided that result in a different melting behaviour of the amplicons themselves. Such amplicons may then for instance differ in length, which makes them amenable for detection using simple gel-electrophoresis. Alternatively, amplicons may also be detected using the 5' nuclease activity of some polymerases (Taqman®). Other real time detection methods are disclosed that do not rely on the destruction of oligonucleotides but instead rely on the use of molecular beacons. Such detection requires a probe containing a fluorophor and a quencher. A third alternative disclosed in EP 1130113 is the use of detection probes consisting of two entities, each being complementary to sequences present on the amplicon each containing a fluorescent moiety wherein fluorescent resonance energy transfer occurs upon binding of both probe entities to the amplicon.

It has now been found that another way of detecting the amplicon provides a more reliable and robust assay that allows for the true multiplexing of up to 30 different target sequences even in a one-tube or two-tube system. This is also referred herein as a closed system as opposed to the above prior art which is inherently an open system. The method according to the invention provides much more freedom to engineer probe assemblies and therefore results in a more reliable assay capable of distinguishing better between a large number of different amplicons.

The invention relates to a method capable of simultaneously detecting a plurality of different target DNA templates in a sample, each DNA template comprising a first target segment and a second target segment, the combination of both target segments being specific for a particular target DNA template, wherein the first and second target-specific segments are essentially adjacent to one another and wherein the first target segment is located 3' from the second target segment, said method comprising the steps of:
 a) an optional reverse transcription and/or pre-amplification step,
 b) bringing at least one DNA template into contact with a plurality of different probe sets, each probe set being specific for one target DNA template and allowing the at least one DNA template to hybridise with a probe set specific for the at least one DNA template,
 c) forming a connected probe assembly comprising the specific probe set,
 d) amplifying the connected probe assembly to obtain at least one amplicon,
 e) detecting the presence of the at least one amplicon by performing a real-time melting curve analysis,
wherein a donor or acceptor label is incorporated in the first or second tag region, essentially adjacent to the detection region and wherein step e) is performed by
 providing a plurality of detection probes comprising
  at least one fluorescent donor label or at least one acceptor label complementary to the label incorporated in the first or second tag region,
  a nucleic acid region specifically hybridisable to said detection sequence
 allowing the at least one amplicon to hybridise with the plurality of detection probes
 monitoring hybridisation of the labelled detection probe at least one pre-selected temperature by measuring the fluorescence of the acceptor label,
wherein said hybridisation of the labelled detection probe is indicative for the presence of a target DNA template in the sample.

The method according to the invention is capable of simultaneously detecting a plurality of different target DNA templates in a sample. This means that the method has the potential of detecting more than one target DNA template in a sample at the same time. If the sample contains only one target DNA template, then the method of course detects that one template, the probes specific for other templates are then not used.

In many clinical samples, sufficient copies of DNA templates are available to perform the method according to the invention without the optional pre-amplification step.

In some clinical samples, however, insufficient copies of a DNA template may be available. In such case, an optional pre-amplification step has to be performed. Also, when the template is an RNA template, this has to be converted into a DNA template by a reverse transcription step. Both these steps are known in the art and the skilled person will be aware of ways to perform them. A schematic overview of this step is provided in FIG. 1. Additional guidance may be found in Sambrook et al., 2000. Molecular Cloning: A Laboratory Manual (Third Edition) Cold Spring Harbor Laboratory Press.

The method according to the invention is then performed by bringing at least one DNA template into contact with a plurality of different probe sets (FIG. 2). This plurality of probe sets is a predetermined set of probes that are specific for a particular set of DNA templates. An advantageous choice of probe sets may be based upon the diversity of agents that are often found together in a clinical disease. For example, for the screening and typing of respiratory tract infections it may be advantageous to combine probe sets specific for influenza virus A and B, parainfluenza virus 1, 2, 3 and 4, respiratory syncytial virus A and B, rhinovirus, coronavirus 229E, OC43 and NL63, human metapneumovirus, adenovirus, *Mycoplasma pneumoniae, Chlamydia pneumoniae, Legionella pneumophila* and *Bordetella pertussis*. Also, the method may be advantageously employed in the detection of infections, like infections in blood. For example, for the screening and typing of blood associated viruses it may be advantageous to combine probe sets for the simultaneous detection of human immunodeficiency virus, hepatitis B virus and hepatitis C virus.

If one or more of the DNA templates for which the probe sets are designed is present in the sample, then the probe set specific for the target DNA template will specifically hybridise with the first and second target segments of the DNA template (FIG. 2).

The skilled person will be aware of the constraints that apply when selecting a suitable region on the DNA template that could serve as first and second target segments. Most importantly, this should be a conserved region so that the natural variability of the template does not cause false-negative results. Additional guidance in the choice of the target regions is to be found in Schouten et al., WO 01/61033, Schouten et al., Nucl. Acids Res. 2002, vol 30 No 12; e57 and Sambrook et al., 2000. Molecular Cloning: A Laboratory Manual (Third Edition) Cold Spring Harbor Laboratory Press.

The specific probe set is then allowed to form a connected probe assembly (FIG. 3). This may be accomplished by a ligase chain reaction which results in multiple copies of the connected probe assembly or by a single ligase step (as depicted in FIG. 3) followed by amplification of the connected probe assembly (FIG. 4). When performing a single ligase step, it may be advantageous to choose a temperature that is not too low, i.e. between 50 and 65° C. T4 ligase performs at temperatures between 42 and 47° C. and is therefore less suitable when a high specificity of the assay is required. It is also advantageous to use the smallest possible volume. Temperature-stabile and temperature-labile ligases are equally suitable. Additional guidance in the choice of suitable ligase enzymes and conditions for its use is to be found in Schouten et al., WO 01/61033, Schouten et al., Nucl. Acids Res. 2002, vol 30 No 12; e57 and Sambrook et al., 2000. Molecular Cloning: A Laboratory Manual (Third Edition) Cold Spring Harbor Laboratory Press.

The detection of the amplified connected probe assembly is advantageously performed in real time (FIG. 5), preferably in a closed system, for instance using fluorescence resonance energy transfer (FRET) probes in a real-time PCR apparatus. To this end, a melting curve analysis may be performed (FIG. 6). In that case, fluorescence is monitored with increasing temperature, a decrease in fluorescence is obtained when probes melt off (For a survey see Mackay et al 2002, Nucleic Acids Res. 30; 1292-1305).

The method according to the invention has a superior sensitivity, even when compared to MLPA. Standard MLPA requires approximately 6000 single copy targets to obtain reproducible results. Samples originating from patients suffering from viral and bacterial infections contain on average much less copies.

In more detail, the invention relates to a method as described above wherein step b) is performed by bringing at least one DNA template into contact with a plurality of different probe sets, each probe set being specific for one target DNA template and allowing the at least one DNA template to hybridise with a probe set specific for the at least one DNA template and each probe set comprising:
   a first nucleic acid probe having
      a first target region hybridisable to the first target segment
      a first tag region, 5' from the first target region comprising a first tag sequence
   a second nucleic acid probe having
      a second target region hybridisable to the second target segment
      a second tag region, 3' from the second target region comprising a second tag sequence
   wherein at least one of the first and second nucleic acid probes contains a detection sequence located 5' from the second tag sequence or located 3' from the first tag sequence.

The invention also relates to a method as described above, wherein step c) is performed by allowing the first and second nucleic acid probes to covalently connect to one another if hybridised to said target DNA template, thereby forming at least one connected probe assembly flanked by the first and second tag regions.

The invention also relates to a method as described above, wherein step d) is performed by:
   allowing the at least one connected probe assembly to contact with a nucleic acid primer pair comprising primer 1 and primer 2, wherein
      primer 1 comprises a first nucleic acid sequence hybridisable to the complement of the first tag sequence and
      primer 2 comprises a second nucleic acid sequence hybridisable to the second tag sequence
   amplification of said at least one connected probe assembly in order to obtain at least one amplicon comprising
      the first tag region or at least part thereof
      the first target region
      the second target region
      the detection region
      the second tag region or at least part thereof
   or the complements thereof.

The invention also relates to a method as described above, wherein step e) is performed by:
   detecting the presence of said at least one amplicon by
      providing a plurality of detection probes comprising
         at least one fluorescent label a nucleic acid region specifically hybridisable to said detection sequence allowing the at least one amplicon to hybridise with the plurality of detection probes monitoring hybridisation of the detection probe at least one pre-selected temperature by measuring the fluorescence of the label, wherein said hybridisation of the detection probe is indicative for the presence of a target DNA template in the sample.

The phrase "simultaneously detecting" as used herein indicates that a plurality, i.e. more than 1, different targets may be detected in one and the same analysis. For that purpose, the method according to the invention provides a different pair of target regions for each nucleic acid template to be amplified. This presupposes that at least part of the nucleic acid sequence of the target DNA template, such as a DNA or RNA virus or the genome of a bacterium, is known. From that known nucleic acid sequence, the skilled person may choose suitable first and second target segments for hybridisation of specific probes. The first and second target segments are preferably long enough to allow hybridisation and annealing of the probes at elevated temperatures, typically about 20 to 40 nucleic acids. The skilled person will take care that the first and second target segments are sufficiently different from each other to allow specific hybridisation with the probe set. For that same reason, the skilled person will choose sufficiently different first and second target segments from the various nucleic acid templates that are to be detected. Means and methods for doing that are readily available in the art and known to the skilled person. Additional guidance in the choice of the target sequences is to be found in Schouten et al., WO 01/61033, Schouten et al., Nucl. Acids Res. 2002, vol 30 No 12; e57 and Sambrook et al., 2000. Molecular Cloning: A Laboratory Manual (Third Edition) Cold Spring Harbor Laboratory Press.

The first and second target segments are chosen essentially adjacent. That means that the first and second nucleic acid probes that hybridise to these regions are positioned such that they may easily couple covalently when a suitable ligase is present. To allow connection of essentially adjacent probes through ligation, one possibility is to generate probes that leave no gap upon hybridisation. However, it is also possible to provide at least one additional single stranded nucleic acid complementary to at least one interadjacent part of said target nucleic acid, whereby hybridisation of said additional nucleic acid to said interadjacent part allows the connecting of two adjacent probes. In this embodiment of the invention a gap upon hybridisation of the probes to the target nucleic acid is filled through the hybridisation of said additional single stranded nucleic acid. Upon connecting and amplification the resulting amplicon will comprise the sequence of said additional single stranded nucleic acid. One may choose to have said interadjacent part to be relatively small thus creating an increased difference in the hybridisation efficiency between said one interadjacent part of said target nucleic acid and a nucleic acid that comprises homology with said one interadjacent part of said target nucleic acid, but comprises a sequence which diverges from in one or more nucleotides. In another embodiment of the invention a gap between probes on said target nucleic acid is filled through extending a 3' end of a hybridised probe or an additional nucleic acid filling part of an interadjacent part, prior to said connecting.

As used herein, the term "complementary" in the context of nucleic acid hybridisation or "complementary nucleic acid" indicates a nucleic acid capable of hybridising to another nucleic acid under normal hybridisation conditions. It may comprise mismatches at a small minority of the sites.

The term "complementary" in the context of a fluorescent label refers to either a donor or acceptor label. A donor label is complementary to an acceptor label and vice versa.

As used herein, "oligonucleotide" indicates any short segment of nucleic acid having a length between 10 up to at least 800 nucleotides. Oligonucleotides can be generated in any matter, including chemical synthesis, restriction endonuclease digestion of plasmids or phage DNA, DNA replication, reverse transcription, or a combination thereof. One or more of the nucleotides can be modified e.g. by addition of a methyl group, a biotin or digoxigenin moiety, a fluorescent tag or by using radioactive nucleotides.

As used herein, the term "primer" refers to an oligonucleotide, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides.

A primer sequence need not reflect the exact sequence of the template. For example, a non-complementary nucleotide fragment may be attached to the 5' end of the primer, with the remainder of the primer sequence being substantially complementary to the strand.

The amplicon obtained in step d) above advantageously comprises the first and second tag regions. Alternatively, the amplicon may also contain only part of the first and second tag regions, depending on the length of the primer pair used. The minimum length of said part of the first and second tag regions as contained in the amplicon corresponds to the lengths of the primers used.

As used herein, the term "target sequence" refers to a specific nucleic acid sequence to be detected and/or quantified in the sample to be analysed.

As used herein, the term "hot-start" refers to methods used to prevent polymerase activity in amplification reactions until a certain temperature is reached.

As used herein, the terms "restriction endonucleases" and "restriction enzymes" refer to bacterial enzymes each of which cut double-stranded DNA at or near a specific nucleotide sequence.

As used herein the term "PCR" refers to the polymerase chain reaction (Mulis et al U.S. Pat. Nos. 4,683,195, 4,683,202 and 4,800,159). The PCR amplification process results in the exponential increase of discrete DNA fragments whose length is defined by the 5' ends of the oligonucleotide primers.

As used herein, the terms "hybridisation" and "annealing" are used in reference to the pairing of complementary nucleic acids.

Conventional techniques of molecular biology and recombinant DNA techniques, which are in the skill of the art, are explained fully in the literature. See, for instance, Sambrook, Fritsch and Maniatis, Molecular Cloning; A Laboratory Manual, Second Edition (1989) and a series, Methods in Enzymology (Academic Press, Inc.) and Sambrook et al., 2000. Molecular Cloning: A Laboratory Manual (Third Edition) Cold Spring Harbor Laboratory Press.

The description of the method according to the invention should not be interpreted so narrowly as that it could not detect other nucleic acid templates, such as RNA templates. A skilled person would understand the disclosure of the present invention as to include the amplification of RNA sequences such as RNA templates, for instance by introducing a preamplification step in order to generate samples containing DNA templates corresponding to RNA sequences in a sample such as a clinical sample. The thus obtained DNA samples could then be used in a method as described above.

Therefore, a method according to the invention as disclosed herein allows for the detection of a plurality of different DNA templates that may be obtained by amplifying a plurality of different nucleic acids such as DNA or RNA in a sample, such as for instance a clinical sample.

Such a method may be particularly advantageous when the plurality of different nucleic acids is derived from micro-organisms, such as bacteria, viruses, algae, parasites, yeasts and fungi. If such micro-organisms are pathogenic, a quick and reliable method that can detect a variety of different nucleic acid templates may be particularly advantageous.

In many circumstances, a sample may contain substances that interfere with a subsequent amplification and/or detection step. In a method according to the invention, such interference may be avoided by extracting the plurality of DNA templates from a sample before hybridisation. Hence, the invention relates to a method as described above, wherein the plurality of DNA templates is extracted from the sample before allowing the DNA templates to hybridise with a plurality of different probes.

In a method according to the invention, tag sequences contained in the first and second nucleic acid probes are used to amplify the first and second target-specific sequences. It may be advantageous when these tag sequences are chosen in such a way that they do not hybridise with any of the target DNA templates that are to be detected. It should be noted that such is not mandatory and that the method may as well be performed without that modification. However sensitivity and specificity of the method are improved in a method as described above wherein at least one of the first and second tag sequences have a nucleic acid sequence chosen in such a way that the first and second tag sequences do not hybridise to the plurality of different target sequences. Typically, a suitable tag sequence has a G/C content of about 50, a length of between approximately 20 to 30 nucleotides and a Tm of 60 to 80° C.

In order to improve specificity and sensitivity of the method, it may also be particularly advantageous that not only the first and/or second tag sequence does not hybridise with any of the target DNA templates that are to be detected, but that the entire tag region does not hybridise. Hence, a method according to the invention relates to a method as described above wherein at least one of the first and second tag regions have a nucleic acid sequence chosen in such a way that the first and second tag regions do not hybridise to the plurality of different target sequences.

The tag sequences in this embodiment of the method according to the invention serve the purpose of amplifying the connected probe assemblies. The tag sequences of the plurality of different probe sets may all be different; however, for reasons of convenience, the tag sequences may advantageously be universal, so that each different connected probe assembly may be amplified with one and the same nucleic acid primer pair. Hence, in one embodiment, the invention relates to a method as described above wherein at least one of the first and second tag sequences is a universal sequence. For the avoidance of doubt, by the above description it is meant that all first tag sequences are identical and that all second tag sequences are identical, not necessarily that the first and second sequences are identical, although that may also be the case without affecting the usefulness of the method.

When both oligonucleotides to be ligated are hybridised to the target nucleic acid, a covalent phosphate link between the two fragments may be formed enzymatically by a ligase. Although other methods of covalently coupling two nucleic acids are available (such as the ligase chain reaction) a method according to the invention is most advantageously performed when the first and second probes are attached to one another by a ligase. In a particular embodiment, the invention therefore relates to a method as described above, wherein the first and second nucleic acid probes are covalently connected to each other in order to form said at least one connected probe assembly by an enzyme having ligase activity.

In one embodiment, probes may be used that hybridise to the template spatially close to each other but not adjacent enough to allow immediate ligation of the probes. In that case, the probe with the target specific sequence at its 3' end can be elongated by a polymerase in the presence of a suitable buffer and the four dNTP's in order to make ligation of the two probes possible. As an alternative the gap between the probes can be filled by complementary oligonucleotides that can be ligated to the probes.

DNA ligases are enzymes capable of forming a covalent phosphate link between two oligonucleotides bound at adjacent sites on a complementary strand. These enzymes use NAD or ATP as a cofactor to seal nicks in double stranded DNA. Alternatively chemical autoligation of modified DNA-ends can be used to ligate two oligonucleotides bound at adjacent sites on a complementary strand (Xu, Y. & Kool, E. T. (1999), Nucleic Acid Res. 27, 875-881).

It can also be envisaged that a method according to the invention may be performed by RNA or DNA primers. DNA primers are more often used for reasons of convenience and because they are more stable than RNA primers. Therefore the invention relates to a method as described above wherein at least one of the nucleic acid primers 1 and primers 2 is a DNA primer.

The detection sequence may be located anywhere between the two tag sequences; however, if the detection sequence is designed to be located essentially adjacent to the first or second tag sequence, it has the least chance of interfering with the hybridisation and/or ligation reactions. This positioning of the detection sequence has the additional advantage that the detection sequence may be used in a detection reaction involving FRET probes. Hence, a method according to the invention may be characterised as a method as described above wherein the detection sequence is essentially adjacent to the first or second tag sequence. In this respect, the term "essentially adjacent" is meant to indicate that energy transfer may occur when an end-labelled probe that hybridises to the detection sequence is capable of energy transfer with a label at the end of the tag sequence. It is even more preferred that the detection sequence is immediately adjacent to the second tag sequence. In the latter case the energy transfer from an internally labelled probe assembly to the fluorescently labelled detection probe is most efficient. In general, energy transfer is optimal when the distance between the labels is less than 5 to 10 nucleotides, preferably less than 5 such as 4, 3, 2, 1 or 0.

The detection sequence may be a random sequence chosen in such a way that it does not interfere with any of the other reagents used in the method, except for the detection probe. Advantageously, the detection sequence is chosen in such a way that the Tm of the detection probe is between 50 and 75° C.

Such a detection method requires the use of internally labelled amplified regions or amplicons. Such amplicons may be obtained by providing labelled primers in a method according to the invention. These primers may then be labelled with a donor or acceptor fluorescent label; conversely the fluorescently labelled detection probe should then of course contain a complementary donor or acceptor fluorescent label. Hence, the invention also relates to a method as described above wherein at least one of primers 1 or primers 2 comprises at least one internal donor or acceptor fluorescent label at or near its 3' end thereby providing at least one internally labelled amplicon upon amplification of said at least one connected probe assembly. It is most preferred to have the label situated at the 3' end of the primer since it will then be in the closest contact with the complementary label of the detection probe. Examples are provided of a method wherein primer 2 comprises the internal label at its 3' end. Also, a method is exemplified wherein said at least one internally labelled amplicon is detected by said plurality of detection probes provided with at least one complementary donor or acceptor fluorescent label at or near its 3' end.

In order to detect the adjacent fluorescent molecules, the donor fluorescent label may be excited and the fluorescence of the acceptor may be measured. The non-adjacent donor and acceptor labels that are still in the reaction vessel do not contribute to the signal because the distance between the donor and the acceptor is too large. In that way, only those DNA templates are detected that allowed the formation of an internally labelled probe assembly (FIG. 5). The method according to the invention thus allows simultaneous real-time detection of a plurality of different DNA templates. A method according to the invention may thus be characterised as a method as described above, wherein the detection of at least one internally labelled amplicon comprises the step of exciting the donor fluorescent label and measuring the fluorescence of the acceptor fluorescent label.

In a particular embodiment, a method according to the invention also provides the opportunity to distinguish a plurality of connected probe assemblies by choosing detection probes in such a way that they can be distinguished by their difference in melting temperature when hybridised to the detection sequence. Such may be accomplished by designing detection probes with a different length or nucleotide composition. Hence, the invention relates to a method as described above, wherein said plurality of detection probes is chosen in such a way that the individual detection probes can be distinguished from each other by their difference in melting temperature when hybridised to the detection sequence.

This embodiment multiples the number of target DNA templates that may be detected. In a real-time assay; melting curves of probes that are only a few degrees Celsius apart may be easily distinguished. Herein we exemplify the use of probes with melting temperatures that are 3 to 5 degrees Celsius apart. Hence, in an advantageous embodiment, the invention relates to a method as described above, wherein the at least one pre-selected temperature consists of a temperature range of at least 3 degrees Celsius and wherein a melting curve analysis is performed to detect a decrease in fluorescence when a detection probe de-hybridises.

In order to further increase the number of target DNA templates that may be detected, different fluorescent labels may be employed. Hence, the invention relates to a method as described above, wherein different fluorescent labels are used to increase the number of different target DNA templates to be detected.

In order to avoid contamination, it may be advantageous to limit the number of times that a reaction vessel has to be opened before the final detection takes place. Due to the specific number and sequence of steps as well as the reaction conditions employed in the present invention, we were able to limit the number of consecutive steps to at most two. In a preferred embodiment, the method according to the invention may even be performed in a single, closed reaction vessel, thus eliminating any risk of contamination. Hence, the invention relates to a method as described above wherein the hybridisation and ligation steps are performed in one reaction vessel.

The present inventors have discovered that the first hybridisation step of the present method may be performed under low salt concentrations and in the presence of Mg ions, preferably $MgCl_2$, thereby allowing the ligation reaction to be performed in the same reaction vessel as the hybridisation reaction. More in particular, the invention relates to a method as described above wherein the hybridisation step is performed in the presence of Mg ions and in the presence of less than 200 mM KCl.

Also, the amplification and ligation step may be performed in one reaction vessel.

If conditions are even further optimised, the entire reaction may be performed even in one reaction vessel. For such a one tube reaction, the following conditions are advantageous. For the amplification step, preferably a hot-start enzyme is used. This has the advantage of providing a longer activation period so that the amplification process allows sufficient time for the hybridisation and ligation steps without interference with the amplification step. This further adds to the reliability of the method and allows for an even increased sensitivity. Hence, the invention relates to a method as described above wherein a hot-start enzyme is used for the amplification step.

A one-tube or one-step reaction is also often referred to as a closed system. This term is used to indicate that a system produces amplicons without the need to reopen the vessel for the addition of reagents, it may also indicate that amplicons are detected in the same vessel without the need to re-open the vessel after the amplification step. Preferably it refers to a system that produces and detects amplicons without the need to open the vessel only once after the addition of the starting reagents. In the context of the present invention, a one-step reaction refers to a reaction wherein at least steps b, c, d and e are performed in one reaction vessel without the need to open the vessel in between these steps, e.g. for the addition or removal of reaction compounds.

A two-tube or two-step reaction may be considered as a semi-closed system. This term indicates that the reaction as described above may be performed in a single reaction vessel wherein the reaction vessel is opened only once in between steps b to e. This is preferably done in between steps b and c.

Mg concentration for the one step assay are preferably chosen between 0.5 and 5 mM and NaCl concentrations are optimal between 0 and 250 mM, preferably between 25 and 150 mM. It is also advantageous when the volume is kept as small as possible, such as between 5 and 25 microliter.

Hence, the invention relates to a method as described above, wherein the hybridisation, ligation and amplification steps are performed in one reaction vessel.

It even proved possible to perform the entire method in a single reaction vessel, i.e. the hybridisation, ligation, amplification and detection step could be combined without the need of opening the reaction vessel even only once. Hence, the invention relates to a method as described above, wherein the detection step is performed in the same vessel as the amplification step.

A method according to the invention may be advantageously employed in any application in which pathogens e.g. viruses, bacteria, fungi, yeasts, algae and parasites and any combination of these pathogens, have to be detected and/or identified. It may also be employed in any application in which pathogens e.g. viruses, bacteria, fungi, parasites have to be typed. It may also be employed in any application in which pathogens e.g. viruses, bacteria, fungi, parasites have to be screened for specific genetic properties.

Specific applications may be found in the screening and typing of *Plasmodium* species in blood of Malaria patients, the detection and identification of *Anopheles* species and the determination of their host preference and screening for sporozoites of *Plasmodium* species, the screening and typing of tick bites associated species like *Ehrlichia* and *Anaplasma* species, the screening and typing of virus infections like enteroviruses, cytomegalovirus and other human herpesviruses in pregnant women, the screening and typing of *Clostridium difficile*, the screening and typing of infections like herpes simplex virus 1 and 2, Varicella zoster virus, cytomegalovirus, enterovirus, parecho virus and Epstein-Barr virus in liquor, the screening and typing of virus infections like human herpesviruses and Epstein Barr virus in cord blood, the screening and typing of human enteric viruses in groundwater, the screening and typing of blood associated viruses like human immunodeficiency virus, hepatitis B virus and hepatitis C virus, the screening and (sub)typing of influenza viruses, the screening for resistance associated polymorphisms in human immunodeficiency viruses and hepatitis viruses, the screening and typing of *mycobacterium* species and identification of the *Mycobacterium tuberculosis* complex members, the screening and typing of human papillomaviruses, the screening and typing of viruses like rice tungro baccilliform virus, rice tungro spherical virus on rice plants affected by rice tungro disease, the screening and typing of *Bordetella pertussis* strains and screening for specific genetic properties, the screening and typing of viruses, bacteria and parasites like human papillomavirus, *Chlamydia trachomatis, Neisseria gonorrhoeae, Mycoplasma genitalium, Trichomonas vaginalis, Treponema pallidum*, commonly associated with sexual transmitted diseases, the screening and typing of *Dermatophyte* species commonly associated with dermatophytosis, the screening and typing of methicillin resistant *Staphylococcus aureus*, the screening and typing of pathogens like *Salmonella* spp., *Campylobacter* spp., Norovirus, commonly associated with foodborne infections and toxications, the screening and typing of pathogens commonly associated with respiratory infections in cattle and pigs, the screening and typing of viruses like noroviruses, rotaviruses, astroviruses, hepatitis A viruses and enteroviruses in oyster samples, the screening and typing of bacteria like mutant streptococci and lactobacilli, commonly associated with dental caries, the screening and typing of tropical diseases (e.g. African trypanosomiasis, dengue fever, leishmaniasis, schistosomiasis, chagas disease, leprosy, lymphatic filariasis, cholera, yellow fever etc.), the screening and typing of zoonoses (e.g. salmonellosis and campylobacteriosis, brucellosis, Rabies, leptospirosis, shigellosis, echinococcosis, toxoplasmosis etc.), the screening and typing of pathogens commonly associated with gastroenteritis (e.g. rotaviruses, noroviruses, adenoviruses, sapoviruses, astroviruses etc.), and the screening and typing of multidrug resistant bacterial strains.

Diagnostic methods for the detection of DNA templates derived from pathogens are often provided in kits. Hence the invention also relates to a kit for performing a method as described above comprising
  a) A plurality of different probe sets
  b) A source of a DNA ligase activity
  c) A source of a DNA polymerase activity
  d) At least one primer comprising at least one donor label
  e) A plurality of detection probes comprising at least one fluorescent label,
  f) Instructions for performing the method.

Depending on the particular embodiment chosen, the kit may comprise additional probes, primers, labelled and unlabelled, as the particular embodiment requires. A particular advantageous kit contains detection probes with different melting temperatures, preferably these detection probes have melting temperatures that differ at least 3 degrees Celsius from each other.

EXAMPLES

The following examples are provided to aid the understanding of the present invention without the intent to limit the invention. It is now within the reach of the skilled artisan to make modifications in the procedures set forth without departing from the spirit of the invention.

In the following examples, a method capable of simultaneously detecting a plurality of different targets in a clinical sample is described. These specific examples, when at least partially combined, form an assay according to the invention that detects a plurality of different pathogens or disease agents in a clinical sample, in this case a nasopharyngeal lavage. The method is capable of simultaneously detecting at least two disease agents selected from the group consisting of influenza A and B, respiratory syncytial virus A and B, human metapneumovirus, *Chlamydia pneumoniae, Mycoplasma pneumoniae* and *Legionella pneumophila*.

Example 1

Design of Probes and Primers

Viral and bacterial sequences were obtained from GenBank and Los Alamos database. Alignments (Clustal X v. 1.8.1) were performed on a set of sequences for each virus to identify highly conserved regions. Since some of the target pathogens are RNA viruses, a reverse transcriptase step followed by pre-amplification step was performed in order to obtain a plurality of different target DNA templates. Based upon these highly conserved regions, reverse transcriptase (RT)-PCR primers and ligation probes were designed. Table 1 lists the target regions, Gen Bank accession numbers and position for the sequences that serve as a template for the hybridisation of the first and second nucleic acid probes.

Conserved regions in the matrix protein gene (M1) were selected as the target for amplification and detection of influenza A virus. These primers are suitable for the amplification of a variety of strains, including, but not limited to, H3N2, H2N2, H4N2, H3N8, H4N6, H6N3, H5N2, H3N6, H6N8, H5N8, H1N1, H7N1, H6N2, H9N2, H6N1, H7N3, H11N1, H5N3, H8N4, H5N1, H4N9, H4N8, H4N1, H10N8, H10N7, H11N6, H12N4, H11N9, H6N6, H2N9, H7N7, H10N5, H12N5, H11N2.

Conserved regions in the matrix protein gene (M1) were also selected as the target for amplification and detection of influenza B virus.

Conserved regions in the major nucleocapsid protein gene (N) were selected as target for amplification and detection of the respiratory syncytial viruses A and B and the human metapneumovirus. Primers used to amplify human metapneumovirus and probes for their detection are suitable for the amplification and detection of all four genetic lineages (A1, A2, B1, B2).

Conserved regions in the major outer membrane gene (OmpA) were selected as the target for amplification and detection of *Chlamydia pneumoniae*.

Conserved regions in the cytadhesin P1 gene (P1) were selected as the target for amplification and detection of *Mycoplasma pneumoniae*.

Conserved regions in the macrophage inhibitor potentiator gene (Mip) were selected as the target for amplification and detection of *Legionella pneumophila*.

Conserved regions in the polyprotein gene (PP) were selected as the target for amplification and detection of encephalomyocarditis virus used as an internal control.

The sequences of the first and second nucleic acid probes used are listed in Table 3. As described above in Table 1 for the primers, these probe sets are suitable for the detection of a variety of strains. For instance, the influenza probes are suitable for the amplification of a variety of strains, including, but not limited to, H3N2, H2N2, H4N2, H3N8, H4N6, H6N3, H5N2, H3N6, H6N8, H5N8, H1N1, H7N1, H6N2, H9N2, H6N1, H7N3, H11N1, H5N3, H8N4, H5N1, H4N9, H4N8, H4N1, H10N8, H10N7, H11N6, H12N4, H11N9, H6N6, H2N9, H7N7, H10N5, H12N5, H11N2. The probes for human metapneumovirus are suitable for the detection of all four genetic lineages.

TABLE 1

Target genes of respiratory viruses and bacteria

| Disease agent | Target gene | Position (nt) | Accession number |
|---|---|---|---|
| Influenza A virus | Matrix protein gene (M1) | 194-264 | CY017444 |
| Influenza B virus | Matrix protein gene (M1) | 44-110 | CY018438 |
| Respiratory syncytial virus A | Major nucleocapsid protein gene (N) | 1142-1221 | U39661 |
| Respiratory syncytial virus B | Major nucleocapsid protein gene (N) | 1352-1434 | AF013254 |
| Human metapneumovirus | Nucleocapsid protein gene (NP) | 483-567 | DQ843658 |
| *Chlamydia pneumoniae* | Major outer membrane gene (OmpA) | 123-201 | AF347608.1 |
| *Mycoplasma pneumoniae* | Cytadhesin P1 gene (P1) | 96-171 | X07191.1 |
| *Legionella pneumophila* | Macrophage inhibitor potentiator gene (Mip) | 25-103 | AF095223.1 |
| Encephalomyocarditis virus = internal amplification control = IAC | Polyprotein gene (PP) | 5164-5227 | X00463.1 |

Table 2 lists the sequence of the RT-PCR primers (forward and reverse) used for reverse transcription and subsequent pre-amplification.

The first and second tag sequences are underlined in Table 3, whereas the target specific regions are not. The detection sequences are in italics.

TABLE 2

RT-PCR primers of respiratory viruses and bacteria

| Disease agent | Primer | Sequence (5'→3') | SEQ ID NO: |
|---|---|---|---|
| Influenza A virus | forward | CAAGACCAATCCTGTCACCTCT | SEQ ID NO: 1 |
| | reverse | ATCGATGGCGCATGCAACTGGCAAG | SEQ ID NO: 2 |
| Influenza B virus | forward | ATGTCGCTGTTTGGAGACACAATTG | SEQ ID NO: 3 |
| | reverse | GCATCTTTTGTTTTTTATCCATTC | SEQ ID NO: 4 |
| Respiratory syncytial virus A | forward | TCCCATAATATACAAGTATGATCTCAA | SEQ ID NO: 5 |
| | reverse | AACCCAGTGAATTTATGATTAGCA | SEQ ID NO: 6 |
| Respiratory syncytial virus B | forward | TGTGGTATGCTATTAATCACTGAAGA | SEQ ID NO: 7 |
| | reverse | GGAGCCACTTCTCCCATCTC | SEQ ID NO: 8 |
| Human metapneumovirus | forward | CAAAGAGGCAAGAAAAACAATGG | SEQ ID NO: 9 |
| | reverse | GCCTGGCTCTTCTGACTGTGGTCTC | SEQ ID NO: 10 |
| *Chlamydia pneumoniae* | forward | GGAACAAAGTCTGCGACCAT | SEQ ID NO: 11 |
| | reverse | AAACAATTTGCATGAAGTCTGAGAA | SEQ ID NO: 12 |
| *Mycoplasma pneumoniae* | forward | GGTTCTTCAGGCTCAGGTCA | SEQ ID NO: 13 |
| | reverse | GGGGTGCGTACAATACCATC | SEQ ID NO: 14 |
| *Legionella pneumophila* | forward | TTAGTGGGCGATTTGTTTTTG | SEQ ID NO: 15 |
| | reverse | ATAGCGTCTTGCATGCCTTT | SEQ ID NO: 16 |
| Internal Amplification control (IAC) | forward | ACATGTAACCGCCCCCATT | SEQ ID NO: 17 |
| | reverse | TCCACGCACGCACTACTATG | SEQ ID NO: 18 |

Primers used to amplify the connected probe assembly are shown in Table 4. The reverse primer carries an internal label.

TABLE 4

| primer 1 and primer 2 | | | | |
|---|---|---|---|---|
| Primers | Label | Position label | Sequence (5'→3') | SEQ ID NO: |
| Forward primer 1 | — | — | GGGTTCCCTAAGGGTTGGA | SEQ ID NO: 37 |
| Reverse primer 2 | FAM | internal label at position 20 | GTGCCAGCAAGATCCAATCTAGA | SEQ ID NO: 38 |

Sequences of Table 3 are described as follows in the Sequence Listing: Influenza A virus—First nucleic acid probe is SEQ ID NO: 19; Influenza A virus—Second nucleic acid probe is SEQ ID NO: 20; Influenza B virus—First nucleic acid probe is SEQ ID NO: 21; Influenza B virus—Second nucleic acid probe is SEQ ID NO: 22; Respiratory syncytial virus A—First nucleic acid probe is SEQ ID NO: 22; Respiratory syncytial virus A—Second nucleic acid probe is SEQ ID NO: 24; Respiratory syncytial virus B—First nucleic acid probe is SEQ ID NO: 25; Respiratory syncytial virus B—Second nucleic acid probe is SEQ ID NO: 26; Human metapneumovirus—First nucleic acid probe is SEQ ID NO: 27; Human metapneumovirus—Second nucleic acid probe is SEQ ID NO: 28; Chlamydia pneumoniae—First nucleic acid probe is SEQ ID NO: 29; Chlamydia pneumoniae—Second nucleic acid probe is SEQ ID NO: 30; Mycoplasma pneumoniae—First nucleic acid probe is SEQ ID NO: 31; Mycoplasma pneumoniae—Second nucleic acid probe is SEQ ID NO: 32; Legionella pneumophila—First nucleic acid probe is SEQ ID NO: 33; Legionella pneumophila—Second nucleic acid probe is SEQ ID NO: 34; Internal Amplification Control (IAC)—First nucleic acid probe is SEQ ID NO: 35; and Internal Amplification Control (IAC)—Second nucleic acid probe is SEQ ID NO: 36.

TABLE 3

First and second nucleic acid probes for the detection of respiratory viruses and bacteria.

| Disease agent | Probe | Sequence (5'→3') |
|---|---|---|
| Influenza A virus | First nucleic acid probe | GGGTTCCCTAAGGGTTGGACCATGCACGCTCACCGTGCCCAGTGAGCGAGG |
| | Second nucleic acid probe | ACTGCAGCGTAGACGCTTTGTCCAAAATGCCCTCAATGGGAATG-ACTAGGAGAGTGGTCA-TCTAGATTGGATCTTGCTGGCAC |
| Influenza B virus | First nucleic acid probe | GGGTTCCCTAAGGGTTGGAGACAGAAGATGGAGAAGGCAAAGCAGA |
| | Second nucleic acid probe | ACTAGCAGAAAAATTACACTGTTGGTTCGGTGGGAAAGAA-ACTAGGAGAGTGGTCA-TCTAGATTGGATCTTGCTGGCAC |
| Respiratory syncytial virus A | First nucleic acid probe | GGGTTCCCTAAGGGTTGGAGGCTCTTAGCAAAGTCAAGTTGAATGATACACTC |
| | Second nucleic acid probe | AACAAAGATCAACTTCTGTCATCCAGCAAATACACCATCCAACGGA-CATGCCTAATGGTCCAGT-TCTAGATTGGATCTTGCTGGCAC |
| Respiratory syncytial virus B | First nucleic acid probe | GGGTTCCCTAAGGGTTGGAGTCCAGGTTAGGAAGGGAAGACACTATAAAGATACTT |
| | Second nucleic acid probe | AAAGATGCTGGATATCATGTTAAAGCTAATGGAGTAGATATAACAA-TCTCCACAGGTAAATCT-TCTAGATTGGATCTTGCTGGCAC |
| Human metapneumovirus | First nucleic acid probe | GGGTTCCCTAAGGGTTGGAGCTCATGCATCCCACAAAATCAGAGGCCTTCAGCACCAG |
| | Second nucleic acid probe | ACACACCAATAATTTTATTATGTGTAGGTGCCTTAATATTCACTAAACTAGCATCAA-ACGGATGCAATAGAACTCTTCGCGC-TCTAGATTGGATCTTGCT |
| Chlamydia pneumoniae | First nucleic acid probe | GGGTTCCCTAAGGGTTGGACCATACATTGGAGTACAATGGTCTCGAGCAACT |
| | Second nucleic acid probe | TTTGATGCTGATAACATCCGCATTGCTCAGCCAAAACTACCTACAG-CAGGTCGTTACGTGGATTAGCGGTC-TCTAGATTGGATCTTGCTGGCAC |
| Mycoplasma pneumoniae | First nucleic acid probe | GGGTTCCCTAAGGGTTGGAGTGGCTTGTGGGGCAGTTACCAAGCAC |
| | Second nucleic acid probe | GAGTGACGGAAACACCTCCTCCACCAACAACCTCGCGCCTAATACT-TCCGTCCTTAGAGTCCGCT-TCTAGATTGGATCTTGCTGGCAC |
| Legionella pneumophila | First nucleic acid probe | GGGTTCCCTAAGGGTTGGAGCTGTTATGGGGCTTGCAATGTCAACAGCAAT |
| | Second nucleic acid probe | GGCTGCAACCGATGCCACATCATTAGCTACAGACAAGGATAAGTIGT-AGCCAGAGTGGTCTTAATG-TCTAGATTGGATCTTGCTGGCAC |
| Internal Amplification | First nucleic acid probe | GGGTTCCCTAAGGGTTGGAGCAGTCAGGTGAGCACCCAGACTTGCCTCCTTGT |

TABLE 3-continued

First and second nucleic acid probes for the
detection of respiratory viruses and bacteria.

| Disease agent | Probe | Sequence (5'→3') |
|---|---|---|
| Control (IAC) | Second nucleic acid probe | GAGAGGCCGCACCTTGGTAGTAAATAGACACATGGCCGAGT-*AGCAGCTTCTGGGCGAAGACC*-<u>TCTAGATTGGATCTTGCTGGCAC</u> |

The sequences and labels of the detection probes used are listed in table 5. Each label was positioned at the 3' end

TABLE 5

Labelled detection probes

| Disease agent | Label | Melting temperature (theoretical) | Sequence (5'→3') | SEQ ID NO: |
|---|---|---|---|---|
| Influenza NB virus | ROX | 55° C. | TGACCACTCTCCTAGT | SEQ ID NO: 39 |
| Respiratory syncytial virus A | ROX | 60° C. | ACTGGACCATTAGGCATG | SEQ ID NO: 40 |
| Respiratory syncytial virus B | Cy5 | 55° C. | AGATTTACCTGTGGAGA | SEQ ID NO: 41 |
| Human metapneumovirus | Cy5 | 70° C. | GCGCGAAGAGTTCTATTGCATCCGT | SEQ ID NO: 42 |
| *Chlamydia pneumoniae* | ROX | 70° C. | GACCGCTAATCCACGTAACGACCTG | SEQ ID NO: 43 |
| *Mycoplasma pneumoniae* | ROX | 65° C. | AGCGGACTCTAAGGACGGA | SEQ ID NO: 44 |
| *Legionella pneumophila* | Cy5 | 60° C. | CATTAAGACCACTCTGGCT | SEQ ID NO: 45 |
| Internal Amplification control (IAC) | IR700 | 65° C. | GGTCTTCGCCCAGAAGCTGCT | SEQ ID NO: 46 |

Each detection probe is specific for a single pathogen as indicated, except for the detection probe for influenza virus, which detects influenza A as well as influenza B.

Example 2

Sample Preparation

A nasopharyngeal lavage was used as clinical specimen. The MagnaPure nucleic acid system (Roche Diagnostics, Almere, The Netherlands) was used as extraction method. The Total nucleic acid isolation kit and the Total nucleic acid lysis extraction MagnaPure protocol were applied. Extractions were performed according to the manufacturer's instructions. Briefly, 200 µl of starting material was used and the purified nucleic acid was eluted in a final volume of 100 µl. Before starting the extraction, 5 µl (approximately 150 copies) of an Internal Amplification Control (IAC) was added to the lysed sample.

Example 3

Pre-Amplification

The extracted nucleic acid with IAC was placed in a separate reaction tube and the mix of primers as shown in table 2 was added along with reagents for reverse-transcription followed by pre-amplification (RT-PCR). While any procedure known in the art for RT-PCR may be used, the following procedure was used in this example. OneStep RT-PCR (Qiagen, Hilden, Germany) was performed in 25 µl containing 5 µl OneStep RT-PCR buffer (12.5 mM MgCl2; pH 8.7 (20° C.)), 1 µl deoxy nucleoside triphosphate (dNTP) mix (containing 1.6 µM of each dNTP), 2.5 µl primermix (containing 2 µM of each primer), 1 µl of OneStep RT-PCR Enzyme mix, 5.5 µl RNase free water and 10 µl of the extracted nucleic acid template with IAC. A blank reaction control was prepared by adding RNase free water to one reaction tube in place of nucleic acid template. The reaction tubes were placed in a Biometra T1 Thermocycler (Biometra, Goëttingen, Germany) programmed as follows: 30 minutes at 50° C. reverse transcription, 15 minutes of initial PCR activation at 95° C. followed by 30 cycli of 30 seconds at 94° C., 30 seconds at 55° C. and 60 seconds at 72° C.

Example 4

Ligation and Detection of a Plurality of Different Target DNA Templates

RT-PCR reactions were 5× diluted after amplification by adding 100 µl TE (10 mM Tris-HCl, 1 mM EDTA pH 8.0) to the individual reaction tubes. Hybridisation was performed in a final volume of 8 µl consisting of 2 µl of five times diluted RT-PCR reaction, buffer components in a final concentration of 0.28 M KCl, 56 mM Tris-HCl pH 8.5, 0.19 mM EDTA, and a complete mix of probes, each probe in a final concentration of 1-4 fmol. The reaction tubes were placed in a Rotor-Gene 6000 real-time system (Corbett, Sydney, Australia) programmed as follows: an initial 5 minutes denaturation step at 98° C. followed by 1 hour at 60° C. hybridisation. Combined ligation and PCR were performed in a final volume of 40 µl consisting of the 8 µl hybridisation reaction, buffer components in a final concentration of 2 mM MgCl2, 3.8 mM Tris-HCl pH 8.2, 0.16 mM NAD, 400 µM of each dNTP), 1 U Ligase-65, 2 U Taq-polymerase, 0.1 µM forward primer, 0.2 µM of an internal FAM-labelled reverse primer, eight 0.1 µM 3' end-labelled detection probes (table 5) and 0.1×SYBR® Green I (Invitrogen, Breda, The Netherlands). The following PCR conditions were used: initial denaturation for 2 min at 95° C., followed by 40 cycles of 30 seconds denaturation at 94° C., 30 seconds of annealing at 60° C. and 1 minute extension at 72° C. Fluorescence was measured at the end of each annealing step. Excitation in each channel was at 470 nm, emission was detected at 510 nm, 610 nm, 660 nm and 710 nm. The addition of 0.1×SYBR Green allows the detection of an amplification curve in the 510 nm channel independent of the label of the detection probe. The amplification program was followed by a melting program. The melting curve was recorded after 2 min of denaturation at 95° C. and re-annealing at 45° C. for 90 s. Fluorescence was detected during heating to 80° C. at 0.2° C./second and a decrease in fluorescence was measured when probes melt off. Fluorescence was measured in four channels. Excitation in each channel was at 470 nm, emission was detected at 510 nm, 610 nm, 660 nm and 710 nm.

The results are presented in FIG. 7. FIG. 7 shows the melt curve analyses of the reaction. The FAM/ROX-channel (470/610 nm) and the FAM/Cy5-channel (470/710 nm) show only background readings and no melting peak is detected. In the FAM/Cy5-channel (470/660 nm) a melting peak is detected at 70° C., corresponding with the melt temperature of the human metapneumovirus detection probe.

Example 5

Detection of Two Different Target DNA Templates in Separate Channels in One Reaction In this example samples containing DNA or in vitro synthesised RNA containing the viral target sequences were used. Reaction 1 contained DNA of *Mycoplasma pneumoniae* and reaction 2 contained RNA with the respiratory syncytial virus A target sequence. Both samples also contained the internal amplification control. The internal amplification control was added in a concentration comparable to the concentration of the sample DNA or RNA. Preamplification and ligation and detection were performed as described in examples 3 and 4. The results of the melt data of the FAM/ROX channel (470/610 nm) and the FAM/IR700 channel (470/710 nm) are shown in FIG. 8. The FAM/ROX channel shows a melting peak in reaction 1 at 65° C. and in reaction 2 at 59° C. This corresponds with the theoretical melting temperatures of the *Mycoplasma pneumoniae* detection probe and the respiratory syncytial virus A detection probe. The FAM/IR700 channel shows in both samples a melting peak at 67° C. This corresponds with the theoretical melting temperature of the detection probe of the internal amplification control.

Example 6

Quantification of Target DNA

In this example quantification of the input DNA concentration based on the amplification curve is demonstrated. A sample containing DNA of *Mycoplasma pneumoniae* is 10 times diluted. Both the undiluted and the diluted sample are analyzed. Pre-amplification and ligation and detection were performed as described in example 3 and 4. FIG. 9 shows the amplification curve and the melt data in the FAM/ROX channel (470/610 nm) of both samples. The analysis of the melt data indicates whether a single product is amplified in the reaction. For both samples only one melting peak is detected in the FAM/ROX channel. The other channels show only background readings. As the detected signal in the FAM/ROX channel is derived from only one product, it's valid to interpret the amplification curve in this channel. The threshold cycle (Ct) for each sample is indicated. The difference in Ct-value between the two samples is 2.2 which corresponds with a fold difference of input DNA of $2^{2.2}=4.6$.

Example 7

Detection of Two Different Target DNA Templates in One Channel

This example gives an impression of the data when two DNA targets are detected in the same channel. The sample preparation, the pre-amplification, the ligation and detection have to be performed as in example 2, 3 and 4. A typical result will look like the result shown in FIG. 10. Two melting peaks at 55° C. and 70° C. can be identified. The channel and the peak at 55° C. correspond with the ROX label and melting temperature of the influenza virus A and B detection probe. The second peak at 70° C. corresponds with the melting temperature of the ROX labelled *C. pneumoniae* detection probe.

Example 8

Hybridisation, Ligation and Detection of a Plurality of Different Target DNA Templates in a Single Closed Reaction Vessel In this example an application is described which is capable of simultaneously detecting a plurality of different targets in clinical samples in a single reaction vessel. In this case a sample containing DNA of *Mycoplasma pneumoniae* is used. The primers and probes are the same as described in example 1, the sample preparation and pre-amplification conditions are as described in examples 2 and 3. RT-PCR reactions were performed from the extracted nucleic acid with IAC and were 5× diluted after amplification by adding 100 µl of 10 mM Tris-HCl, 1 mM EDTA pH 8.0 to the individual reaction tubes. The entire method is preformed in a single reaction vessel and hybridisation, ligation, amplification and detection is combined in one procedural step without opening the reaction vessel. Reaction mixture was prepared in 20 µl consisting of 2 µl of five times diluted RT-PCR reaction, buffer components in a final concentration of 3 mM MgCl2, 10 mM Tris-HCl pH 8.2, 0.2 mM NAD, 50 mM KCl, 200 µM of each dNTP, a complete mix of probes, each probe in a final concentration of 1-4 fmol, 0.1 µM forward primer, 0.2 µM of an internal FAM-labelled reverse primer, 1 U Taq-ligase, 0.5 U HotStarTaq DNA polymerase (Qiagen, Hilden Germany), eight 3' end-labelled detection probes (0.1 µM of each probe) (table 5) and 0.1×SYBR® Green I (Invitrogen, Breda, The Netherlands). The reaction tubes were placed in a Rotor-Gene 6000 real-time system (Corbett, Sydney, Australia) programmed as follows: an initial 5 minutes denaturation step at 98° C. followed by 1 hour at 60° C. hybridisation, a denaturation and initial activation of the hotstart Taq polymerase for 15 min at 95° C., followed by 40 cycles of 30 s denaturation at 94° C., 30 s of annealing at 60° C. and 1 min extension at 72° C. Fluorescence was measured at the end of each annealing step. Excitation in each channel was at 470 nm, emission was detected at 510 nm, 610 nm, 660 nm and 710 nm. The addition of 0.1×SYBR Green allows the detection of an amplification curve in the 510 nm channel independent of the label of the detection probe. The amplification program was followed by a melting program. The melting curve was recorded after 2 min of denaturation at 95° C. and reannealing at 45° C. for 90 s. Fluorescence was detected during heating to 80° C. at 0.2° C./s and a decrease in fluorescence was measured when probes melt off. Fluorescence was measured in four channels. Excitation in each channel was at 470 nm, emission was detected at 510 nm, 610 nm, 660 nm and 710 nm. The result of a melt curve analysis in the FAM/ROX channel (470/610 nm) is shown in FIG. 11. The data shows a melting peak at 64.1° C., which corresponds with the melting temperature of the *Mycoplasma pneumoniae* detection probe. The other channels showed background readings.

Example 9

Clinical Validation

A total of 128 clinical specimens were analysed with a method according to the invention. Probe sets against influenza virus A, B and A subtype $H5N_1$, parainfluenza virus 1, 2, 3 and 4, respiratory syncytial virus A and B, rhinovirus, coronavirus 229E, OC43 and NL63, adenovirus and human metapneumovirus were used. The sensitivity of this multiparameter respiratory test was as good as monoplex real-time PCR for each individual virus. Identification of the amplified products was by melting curve analysis using detection probes in a closed system.

The invention claimed is:

1. A method for detecting and differentiating a plurality of pathogenic organisms having a copy number of less than 6000 in a clinical sample in a single reaction vessel, the clinical sample comprising a plurality of different target RNA templates and/or a plurality of different target DNA templates derived from the plurality of pathogenic organisms, each target DNA template comprising a first target segment and a second target segment, the combination of both the first target segment and the second target segment being specific for a particular target DNA template, wherein the first target segment and the second target segment are essentially adjacent to one another and wherein the first target segment is located 3' from the second target segment, said method comprising the steps of:
   (a) a reverse transcription step in the single reaction vessel of the plurality of different target RNA templates into the plurality of different target DNA templates and/or an optional pre-amplification step of the plurality of different target DNA templates in the single reaction vessel;
   (b) bringing said plurality of different target DNA templates into contact with a plurality of different probe sets in the single reaction vessel, each probe set being specific for a particular target DNA template of the plurality of different target DNA templates and allowing the particular target DNA template to hybridise thereto, each probe set comprising:
      a first nucleic acid probe having a first target region hybridisable to the first target segment of said particular target DNA template and a first tag region, wherein the first tag region is located 5' from the first target region and comprises a first tag sequence, and
      a second nucleic acid probe having a second target region hybridisable to the second target segment of said particular target DNA template and a second tag region, wherein the second tag region is located 3' from the second target region and comprises a second tag sequence, and wherein at least one of the first nucleic acid probe or the second nucleic acid probe contains a detection sequence located 5' from the second tag sequence or located 3' from the first tag sequence;
   (c) forming a plurality of connected probe assemblies in the single reaction vessel, wherein the plurality of connected probe assemblies comprises the plurality of different probe sets and is formed by ligating said first nucleic acid probe and said second nucleic acid probe of each probe set;
   (d) amplifying the plurality of connected probe assemblies in the single reaction vessel to obtain a plurality of amplicons, wherein the plurality of connected probe assemblies are amplified by allowing the plurality of connected probe assemblies to contact with a plurality of nucleic acid primer pairs, each nucleic acid primer pair comprising:
      a primer 1 and a primer 2, wherein at least one of primer 1 or primer 2 comprises at least one internal donor or acceptor fluorescent label at or near its 3' end, thereby providing a plurality of internally labelled amplicons upon amplification of said plurality of connected probe assemblies, wherein the internal donor or acceptor fluorescent label is incorporated in the first or second tag region and is essentially adjacent to the detection sequence; and (e) detecting and differentiating the plurality of internally labelled amplicons in the single reaction vessel, wherein the plurality of internally labelled amplicons are detected and differentiated by performing a real-time melting curve analysis comprising:

(1) providing a plurality of labelled detection probes, each labelled detection probe being specific for a particular detection sequence of a particular internally labelled amplicon and comprising:

at least one fluorescent donor or acceptor label complementary to the internal donor or acceptor fluorescent label incorporated in the first or second tag region by said plurality of nucleic acid primer pairs, wherein a single pair of donor and acceptor labels is used in detecting a plurality of internally labelled amplicons, wherein each similarly labelled detection probe exhibits a different melting temperature upon hybridisation to the particular detection sequence of the particular internally labelled amplicon, such that the plurality of internally labelled amplicons is distinguishable; and a nucleic acid region specifically hybridisable to said particular detection sequence of the particular internally labelled amplicon, (2) allowing the plurality of internally labelled amplicons to hybridise with the plurality of labelled detection probes, and (3) monitoring hybridisation and the different melting temperatures of the plurality of labelled detection probes by measuring the fluorescence of the acceptor labels over a pre-selected increasing temperature range within different fluorescent detection channels, wherein:

said hybridisation of the plurality of labelled detection probes is indicative for the presence of the plurality of different pathogenic organisms in the clinical sample, the different melting temperatures in combination with the different fluorescent labels of the plurality of labelled detection probes allow detection and distinguishability of a plurality of different pathogenic organisms in the clinical sample, such that up to about 30 different pathogenic organisms in the clinical sample may be detected and distinguished; and steps (a)-(e) are performed in a closed system.

2. The method according to claim 1 wherein step (c) is performed by:

allowing the first nucleic acid probe and the second nucleic acid probe of each probe set to covalently connect to one another if hybridised to said plurality of different target DNA templates, thereby forming the plurality of connected probe assemblies, wherein each of the plurality of connected probe assemblies is flanked by the first and second tag regions.

3. The method according to claim 1 wherein step (d) is performed in order to obtain a plurality of amplicons comprising:
the first tag region or part thereof,
the first target region,
the second target region,
the detection region, and
the second tag region or part thereof,
or the complements thereof.

4. The method according to claim 1 wherein the plurality of different target DNA templates is obtained by amplifying a plurality of different nucleic acids in the clinical sample.

5. The method according to claim 1 wherein the plurality of different target DNA templates is extracted from the clinical sample before allowing the plurality of different target DNA templates to hybridise with said plurality of different probe sets.

6. The method according to claim 1 wherein at least one of the first and second tag sequences have a nucleic acid sequence chosen in such a way that the first and second tag sequences do not hybridise to the plurality of different target DNA templates.

7. The method according to claim 1 wherein at least one of the first and second tag regions have a nucleic acid sequence chosen in such a way that the first and second tag regions do not hybridise to the plurality of different target DNA templates.

8. The method according to claim 1 wherein at least one of the first and second tag sequences are universal sequences.

9. The method according to claim 1 wherein the first and second nucleic acid probes are covalently connected to each other in order to form said plurality of connected probe assemblies by an enzyme having ligase activity.

10. The method according to claim 1 wherein at least one of primer 1 or primer 2 is a DNA primer.

11. The method according to claim 1 wherein the detection sequence is immediately adjacent to the second tag sequence.

12. The method according to claim 1 wherein primer 2 comprises the internal donor or acceptor fluorescent label at or near its 3' end.

13. The method according to claim 12 wherein the detection of the plurality of internally labelled amplicons comprises the step of exciting the donor fluorescent label and measuring the fluorescence of the acceptor fluorescent label.

14. The method according to claim 1 wherein said plurality of labelled detection probes is chosen in such a way that the individual detection probes can be distinguished from each other by their difference in length or nucleotide composition.

15. The method according to claim 1 wherein the pre-selected increasing temperature range consists of a temperature range defined by the different melting temperatures of the plurality of labelled detection probes being at least 3 degrees Celsius apart and wherein the melting curve analysis is performed to detect a decrease in fluorescence when a labelled detection probe de-hybridises.

16. The method according to claim 1 wherein hybridisation in step (b) is performed in the presence of Mg ions and in the presence of less than 200 mM KCl.

17. The method according to claim 1 wherein a hot-start enzyme is used for amplification in step (d).

* * * * *

SEQUENCE LISTING

```
<160> NUMBER OF SEQ ID NOS: 46

<210> SEQ ID NO 1
<211> LENGTH: 22
<212> TYPE: DNA
<213> ORGANISM: Artificial
<220> FEATURE:
<223> OTHER INFORMATION: Artificial primer or probe

<400> SEQUENCE: 1
caagaccaat cctgtcacct ct                                              22

<210> SEQ ID NO 2
<211> LENGTH: 25
<212> TYPE: DNA
<213> ORGANISM: Artificial
<220> FEATURE:
<223> OTHER INFORMATION: Artificial primer or probe

<400> SEQUENCE: 2
atcgatggcg catgcaactg gcaag                                           25

<210> SEQ ID NO 3
<211> LENGTH: 25
<212> TYPE: DNA
<213> ORGANISM: Artificial
<220> FEATURE:
<223> OTHER INFORMATION: Artificial primer or probe

<400> SEQUENCE: 3
atgtcgctgt ttggagacac aattg                                           25

<210> SEQ ID NO 4
<211> LENGTH: 24
<212> TYPE: DNA
<213> ORGANISM: Artificial
<220> FEATURE:
<223> OTHER INFORMATION: Artificial primer or probe

<400> SEQUENCE: 4
gcatcttttg tttttatcc attc                                             24

<210> SEQ ID NO 5
<211> LENGTH: 27
<212> TYPE: DNA
<213> ORGANISM: Artificial
<220> FEATURE:
```

<223> OTHER INFORMATION: Artificial primer or probe

<400> SEQUENCE: 5
tcccataata tacaagtatg atctcaa                                27

<210> SEQ ID NO 6
<211> LENGTH: 24
<212> TYPE: DNA
<213> ORGANISM: Artificial
<220> FEATURE:
<223> OTHER INFORMATION: Artificial primer or probe

<400> SEQUENCE: 6
aacccagtga atttatgatt agca                                   24

<210> SEQ ID NO 7
<211> LENGTH: 26
<212> TYPE: DNA
<213> ORGANISM: Artificial
<220> FEATURE:
<223> OTHER INFORMATION: Artificial primer or probe

<400> SEQUENCE: 7
tgtggtatgc tattaatcac tgaaga                                 26

<210> SEQ ID NO 8
<211> LENGTH: 20
<212> TYPE: DNA
<213> ORGANISM: Artificial
<220> FEATURE:
<223> OTHER INFORMATION: Artificial primer or probe

<400> SEQUENCE: 8
ggagccactt ctcccatctc                                        20

<210> SEQ ID NO 9
<211> LENGTH: 23
<212> TYPE: DNA
<213> ORGANISM: Artificial
<220> FEATURE:
<223> OTHER INFORMATION: Artificial primer or probe

<400> SEQUENCE: 9
caaagaggca agaaaaacaa tgg                                    23

<210> SEQ ID NO 10
<211> LENGTH: 25
<212> TYPE: DNA
<213> ORGANISM: Artificial
<220> FEATURE:
<223> OTHER INFORMATION: Artificial primer or probe

<400> SEQUENCE: 10
gcctggctct tctgactgtg gtctc                                  25

<210> SEQ ID NO 11
<211> LENGTH: 20
<212> TYPE: DNA
<213> ORGANISM: Artificial
<220> FEATURE:
<223> OTHER INFORMATION: Artificial primer or probe

<400> SEQUENCE: 11
ggaacaaagt ctgcgaccat                                        20

```
<210> SEQ ID NO 12
<211> LENGTH: 25
<212> TYPE: DNA
<213> ORGANISM: Artificial
<220> FEATURE:
<223> OTHER INFORMATION: Artificial primer or probe

<400> SEQUENCE: 12
aaacaatttg catgaagtct gagaa                                           25

<210> SEQ ID NO 13
<211> LENGTH: 20
<212> TYPE: DNA
<213> ORGANISM: Artificial
<220> FEATURE:
<223> OTHER INFORMATION: Artificial primer or probe

<400> SEQUENCE: 13
ggttcttcag gctcaggtca                                                 20

<210> SEQ ID NO 14
<211> LENGTH: 20
<212> TYPE: DNA
<213> ORGANISM: Artificial
<220> FEATURE:
<223> OTHER INFORMATION: Artificial primer or probe

<400> SEQUENCE: 14
ggggtgcgta caataccatc                                                 20

<210> SEQ ID NO 15
<211> LENGTH: 21
<212> TYPE: DNA
<213> ORGANISM: Artificial
<220> FEATURE:
<223> OTHER INFORMATION: Artificial primer or probe

<400> SEQUENCE: 15
ttagtgggcg atttgttttt g                                               21

<210> SEQ ID NO 16
<211> LENGTH: 20
<212> TYPE: DNA
<213> ORGANISM: Artificial
<220> FEATURE:
<223> OTHER INFORMATION: Artificial primer or probe

<400> SEQUENCE: 16
atagcgtctt gcatgccttt                                                 20

<210> SEQ ID NO 17
<211> LENGTH: 19
<212> TYPE: DNA
<213> ORGANISM: Artificial
<220> FEATURE:
<223> OTHER INFORMATION: Artificial primer or probe

<400> SEQUENCE: 17
acatgtaacc gcccccatt                                                  19

<210> SEQ ID NO 18
<211> LENGTH: 20
<212> TYPE: DNA
<213> ORGANISM: Artificial
<220> FEATURE:
<223> OTHER INFORMATION: Artificial primer or probe
```

<400> SEQUENCE: 18
tccacgcacg cactactatg                                                    20

<210> SEQ ID NO 19
<211> LENGTH: 51
<212> TYPE: DNA
<213> ORGANISM: Artificial
<220> FEATURE:
<223> OTHER INFORMATION: Artificial primer or probe

<400> SEQUENCE: 19 gggttccta agggttggac catgcacgct caccgtgccc agtgagcgag g                  51

<210> SEQ ID NO 20
<211> LENGTH: 83
<212> TYPE: DNA
<213> ORGANISM: Artificial
<220> FEATURE:
<223> OTHER INFORMATION: Artificial primer or probe

<400> SEQUENCE: 20
actgcagcgt agacgctttg tccaaaatgc cctcaatggg aatgactagg agagtggtca        60
tctagattgg atcttgctgg cac                                                83

<210> SEQ ID NO 21
<211> LENGTH: 46
<212> TYPE: DNA
<213> ORGANISM: Artificial
<220> FEATURE:
<223> OTHER INFORMATION: Artificial primer or probe

<400> SEQUENCE: 21 gggttccta agggttggag acagaagatg gagaaggcaa agcaga                        46

<210> SEQ ID NO 22
<211> LENGTH: 79
<212> TYPE: DNA
<213> ORGANISM: Artificial
<220> FEATURE:
<223> OTHER INFORMATION: Artificial primer or probe

<400> SEQUENCE: 22
actagcagaa aaattacact gttggttcgg tgggaaagaa actaggagag tggtcatcta        60
gattggatct tgctggcac                                                     79

<210> SEQ ID NO 23
<211> LENGTH: 53
<212> TYPE: DNA
<213> ORGANISM: Artificial
<220> FEATURE:
<223> OTHER INFORMATION: Artificial primer or probe

<400> SEQUENCE: 23 gggttccta agggttggag gctcttagca aagtcaagtt gaatgataca ctc                53

<210> SEQ ID NO 24
<211> LENGTH: 87
<212> TYPE: DNA
<213> ORGANISM: Artificial
<220> FEATURE:
<223> OTHER INFORMATION: Artificial primer or probe

<400> SEQUENCE: 24
aacaaagatc aacttctgtc atccagcaaa tacaccatcc aacggacatg cctaatggtc        60
cagttctaga ttggatcttg ctggcac                                          87

<210> SEQ ID NO 25
<211> LENGTH: 56
<212> TYPE: DNA
<213> ORGANISM: Artificial
<220> FEATURE:
<223> OTHER INFORMATION: Artificial primer or probe

<400> SEQUENCE: 25
gggttcccta agggttggag tccaggttag gaagggaaga cactataaag atactt          56

<210> SEQ ID NO 26
<211> LENGTH: 86
<212> TYPE: DNA
<213> ORGANISM: Artificial
<220> FEATURE:
<223> OTHER INFORMATION: Artificial primer or probe

<400> SEQUENCE: 26
aaagatgctg gatatcatgt taaagctaat ggagtagata taacaatctc cacaggtaaa      60
tcttctagat tggatcttgc tggcac                                           86

<210> SEQ ID NO 27
<211> LENGTH: 58
<212> TYPE: DNA
<213> ORGANISM: Artificial
<220> FEATURE:
<223> OTHER INFORMATION: Artificial primer or probe

<400> SEQUENCE: 27
gggttcccta agggttggag ctcatgcatc ccacaaaatc agaggccttc agcaccag        58

<210> SEQ ID NO 28
<211> LENGTH: 105
<212> TYPE: DNA
<213> ORGANISM: Artificial
<220> FEATURE:
<223> OTHER INFORMATION: Artificial primer or probe

<400> SEQUENCE: 28
acacaccaat aattttatta tgtgtaggtg ccttaatatt cactaaacta gcatcaaacg      60
gatgcaatag aactcttcgc gctctagatt ggatcttgct ggcac                      105

<210> SEQ ID NO 29
<211> LENGTH: 52
<212> TYPE: DNA
<213> ORGANISM: Artificial
<220> FEATURE:
<223> OTHER INFORMATION: Artificial primer or probe

<400> SEQUENCE: 29
gggttcccta agggttggac catacattgg agtacaatgg tctcgagcaa ct              52

<210> SEQ ID NO 30
<211> LENGTH: 94
<212> TYPE: DNA
<213> ORGANISM: Artificial
<220> FEATURE:
<223> OTHER INFORMATION: Artificial primer or probe

<400> SEQUENCE: 30
tttgatgctg ataacatccg cattgctcag ccaaaactac ctacagcagg tcgttacgtg      60
gattagcggt ctctagattg gatcttgctg gcac                              94

<210> SEQ ID NO 31
<211> LENGTH: 46
<212> TYPE: DNA
<213> ORGANISM: Artificial
<220> FEATURE:
<223> OTHER INFORMATION: Artificial primer or probe

<400> SEQUENCE: 31
gggttcccta agggttggag tggcttgtgg ggcagttacc aagcac                 46

<210> SEQ ID NO 32
<211> LENGTH: 88
<212> TYPE: DNA
<213> ORGANISM: Artificial
<220> FEATURE:
<223> OTHER INFORMATION: Artificial primer or probe

<400> SEQUENCE: 32
gagtgacgga aacacctcct ccaccaacaa cctcgcgcct aatacttccg tccttagagt  60
ccgcttctag attggatctt gctggcac                                     88

<210> SEQ ID NO 33
<211> LENGTH: 51
<212> TYPE: DNA
<213> ORGANISM: Artificial
<220> FEATURE:
<223> OTHER INFORMATION: Artificial primer or probe

<400> SEQUENCE: 33
gggttcccta agggttggag ctgttatggg gcttgcaatg tcaacagcaa t           51

<210> SEQ ID NO 34
<211> LENGTH: 89
<212> TYPE: DNA
<213> ORGANISM: Artificial
<220> FEATURE:
<223> OTHER INFORMATION: Artificial primer or probe

<400> SEQUENCE: 34
ggctgcaacc gatgccacat cattagctac agacaaggat aagttgtagc cagagtggtc  60
ttaatgtcta gattggatct tgctggcac                                    89

<210> SEQ ID NO 35
<211> LENGTH: 53
<212> TYPE: DNA
<213> ORGANISM: Artificial
<220> FEATURE:
<223> OTHER INFORMATION: Artificial primer or probe

<400> SEQUENCE: 35
gggttcccta agggttggag cagtcaggtg agcacccaga cttgcctcct tgt         53

<210> SEQ ID NO 36
<211> LENGTH: 85
<212> TYPE: DNA
<213> ORGANISM: Artificial
<220> FEATURE:
<223> OTHER INFORMATION: Artificial primer or probe

<400> SEQUENCE: 36
gagaggccgc accttggtag taaatagaca catggccgag tagcagcttc tgggcgaaga  60
cctctagatt ggatcttgct ggcac                                        85

<210> SEQ ID NO 37
<211> LENGTH: 19
<212> TYPE: DNA
<213> ORGANISM: Artificial
<220> FEATURE:
<223> OTHER INFORMATION: Artificial primer or probe

<400> SEQUENCE: 37
gggttcccta agggttgga                                                    19

<210> SEQ ID NO 38
<211> LENGTH: 23
<212> TYPE: DNA
<213> ORGANISM: Artificial
<220> FEATURE:
<223> OTHER INFORMATION: Artificial primer or probe

<400> SEQUENCE: 38
gtgccagcaa gatccaatct aga                                               23

<210> SEQ ID NO 39
<211> LENGTH: 16
<212> TYPE: DNA
<213> ORGANISM: Artificial
<220> FEATURE:
<223> OTHER INFORMATION: Artificial primer or probe

<400> SEQUENCE: 39
tgaccactct cctagt                                                       16

<210> SEQ ID NO 40
<211> LENGTH: 18
<212> TYPE: DNA
<213> ORGANISM: Artificial
<220> FEATURE:
<223> OTHER INFORMATION: Artificial primer or probe

<400> SEQUENCE: 40
actggaccat taggcatg                                                     18

<210> SEQ ID NO 41
<211> LENGTH: 17
<212> TYPE: DNA
<213> ORGANISM: Artificial
<220> FEATURE:
<223> OTHER INFORMATION: Artificial primer or probe

<400> SEQUENCE: 41
agatttacct gtggaga                                                      17

<210> SEQ ID NO 42
<211> LENGTH: 25
<212> TYPE: DNA
<213> ORGANISM: Artificial
<220> FEATURE:
<223> OTHER INFORMATION: Artificial primer or probe

<400> SEQUENCE: 42
gcgcgaagag ttctattgca tccgt                                             25

<210> SEQ ID NO 43
<211> LENGTH: 25
<212> TYPE: DNA
<213> ORGANISM: Artificial
<220> FEATURE:

```
<223> OTHER INFORMATION: Artificial primer or probe

<400> SEQUENCE: 43
gaccgctaat ccacgtaacg acctg                                        25

<210> SEQ ID NO 44
<211> LENGTH: 19
<212> TYPE: DNA
<213> ORGANISM: Artificial
<220> FEATURE:
<223> OTHER INFORMATION: Artificial primer or probe

<400> SEQUENCE: 44
agcggactct aaggacgga                                               19

<210> SEQ ID NO 45
<211> LENGTH: 19
<212> TYPE: DNA
<213> ORGANISM: Artificial
<220> FEATURE:
<223> OTHER INFORMATION: Artificial primer or probe

<400> SEQUENCE: 45
cattaagacc actctggct                                               19

<210> SEQ ID NO 46
<211> LENGTH: 21
<212> TYPE: DNA
<213> ORGANISM: Artificial
<220> FEATURE:
<223> OTHER INFORMATION: Artificial primer or probe

<400> SEQUENCE: 46
ggtcttcgcc cagaagctgc t                                            21
```